(12) United States Patent
Tarasova et al.

(10) Patent No.: US 7,517,849 B1
(45) Date of Patent: Apr. 14, 2009

(54) INHIBITION OF ABC TRANSPORTERS BY TRANSMEMBRANE DOMAIN ANALOGS

(75) Inventors: Nadya I. Tarasova, Frederick, MD (US); Christopher J. Michejda, North Potomac, MD (US); Michael M. Gottesman, Bethesda, MD (US); Christine A. Hrycyna, Lafayette, IN (US)

(73) Assignee: The United States of America as represented by the Secretary of Health and Human Services, Washington, DC (US)

( * ) Notice: Subject to any disclaimer, the term of this patent is extended or adjusted under 35 U.S.C. 154(b) by 1244 days.

(21) Appl. No.: 10/130,192

(22) PCT Filed: Nov. 17, 2000

(86) PCT No.: PCT/US00/31817

§ 371 (c)(1),
(2), (4) Date: May 13, 2002

(87) PCT Pub. No.: WO01/36477

PCT Pub. Date: May 25, 2001

Related U.S. Application Data

(60) Provisional application No. 60/166,767, filed on Nov. 22, 1999, provisional application No. 60/166,382, filed on Nov. 18, 1999.

(51) Int. Cl.
| | |
|---|---|
| *A61K 38/00* | (2006.01) |
| *C07K 5/00* | (2006.01) |
| *G01N 33/53* | (2006.01) |
| *C07K 14/00* | (2006.01) |

(52) U.S. Cl. .................. 514/2; 530/300; 530/350; 435/7.1; 435/7.2

(58) Field of Classification Search ........... 530/300
See application file for complete search history.

(56) References Cited

U.S. PATENT DOCUMENTS

| | | | | |
|---|---|---|---|---|
| 5,350,836 | A | * | 9/1994 | Kopchick et al. ........... 530/399 |
| 7,105,488 | B1 | | 9/2006 | Tarasova et al. |

FOREIGN PATENT DOCUMENTS

| | | | |
|---|---|---|---|
| CA | WO 97/35881 | * | 10/1997 |
| WO | WO 99/43711 A1 | | 9/1999 |

OTHER PUBLICATIONS

Seebohm, et al, 2005, J. Physiol., 563.2: 359-368.*
Putnam, et al, 2000, Microb. Mol. Biol. Rev., 64(4): 672-693.*
Gros, et al, 1991, Proc. Natl. Acad. Sci. 88: 7289-7293.*
Jain, R., 1994, Barriers to Drug Delivery in Solid Tumors, Sci. Amer., 271(1): 58-65.*
Curti, B., 1993, Crit. Rev. Oncol./Hematol., 14: 29-39.*

\* cited by examiner

*Primary Examiner*—Elizabeth C. Kemmerer
*Assistant Examiner*—Sandra Wegert
(74) *Attorney, Agent, or Firm*—Townsend and Townsend and Crew LLP

(57) ABSTRACT

ATP-binding cassette (ABC) transporters generally contain a number of transmembrane helices. The present invention provides synthetic peptides derived from these transmembrane helices. The peptides inhibit ABC transporter function, presumably by disrupting the structure of the ABC transporter. Negatively charged residues are added at the extracellular terminus to promote correct orientation of the peptide in the membrane, and residues considered to aid solubility may be added at that terminus to increase solubility. Exemplary ABC transporters that can be inhibited by these peptides include MDR1, MRP1, MRP2 and BCRP. The invention further provides nucleic acids encoding the peptides, expression cassettes comprising the nucleic acids, and host cells expressing the expression cassettes. The invention further provides a simple and inexpensive assay for determining whether a potential chemotherapeutic agent can inhibit the activity of P-gly-coprotein.

39 Claims, 2 Drawing Sheets

```
1                                                                                    TM1
MDLEGDRNGG AKKKN̶F̶F̶K̶L̶N̶ NKSEKDKKEK KPTVSVFSMF RYSNWLDKLY MVVGTLAAII
61
HGAGLPLMML VFGEMTDIFA NAGNLEDLMS NITNRSDIND TGFFMNLEEDMTRYAYYYSG
121        TM2
IGAGVLVAAY IQVSFWCLAA GRQIHKIRKQ FFHAIMRQEI GWFDVHDVGE LNTRLTDDVS
181                     TM3                   TM4
KINEGIGDKI GMFFQSMATF FTGFIVGFIR GWKLTLVILA ISPVLGLSAA VWAKILSSFT
241
DKELLAYAKA GAVAEEVLAA IRTVIAFGGQ KKELERYNKN LEEAKRIGIK KAITANISIG
301 TM5                              TM6
AAFLLIYASY ALAFWYGTTL VLSGEYSIGQ VLTVFFSVLI GAFSVGQASP SIEAFANARG
361
AAYEIFKIID NKPSIDSYSK SGHKPDNIKG NLEFRNVHFS YPSRKEVKIL KGLNLKVQSG
421
QTVALVGNSG CGKSTTVQLM QRLYDPTEGM VSVDGQDIRT INVRFLREII GVVSQEPVLF
481
ATTIAENIRY GRENVTMDEI EKAVKEANAY DFIMKLPHKF DTLVGERGAQ LSGGQKQRIA
541
IARALVRNPK ILLLDEATSA LDTESEAVVQ VALDKARKGR TTTVIAHRLS TVRNADVIAG
601
FDDGVIVEKG NHDELMKEKG IYFKLVTMQT AGNEVELENA ADESKSEIDA LEMSSNDSRS
661                                                                    TM7
SLIRKRSTRR SVRGSQAQDR KLSTKEALDE SIPPVSFWRI MKLNLTEWPY FVVGVFCAII
721                                           TM8
NGGLQPAFAI IFSKIIGVFT RIDDPETKRQ NSNLFSLLFL ALGIISFITF FLQGFTFGKA
781                                                                    TM9
GEILTKRLRY MVFRSMLRQD VSWFDDPKNT TGALTTRLAN DAAQVKGAIG SRLAVITQNI
841                                  TM10
ANLGTGIIIS FIYGWQLTLL LLAIVPIIAI AGVVEMKMLS GQALKDKKEL EGAGKIATEA
901                                                                    TM11
IENFRTVVSL TQEQKFEHMY AQSLQVPYRN SLRKAHIFGI TFSFTQAMMY FSYAGCFRFG
961                     TM12
AYLVAHKLMS FEDVLLVFSA VVFGAMAVGQ VSSFAPDYAK AKISAAHIIM IIEKTPLIDS
1021
YSTEGLMPNT LEGNVTFGEV VFNYPTRPDI PVLQGLSLEV KKGQTLALVG SSGCGKSTVV
1081
QLLERFYDPL AGKVLLDGKE IKRLNVQWLR AHLGIVSQEP ILFDCSIAEN IAYGDNSRVV
1141
SQEEIVRAAK EANIHAFIES LPNKYSTKVG DKGTQLSGGQ KQRIAIARAL VRQPHILLLD
1201
EATSALDTES EKVVQEALDK AREGRTCIVI AHRLSTIQNA DLIVVFQNGR VKEHGTHQQL
1261
LAQKGIYFSM VSVQAGTKRQ
```

Figure 1

MSSSNVEVFI PVSQGNTNGF PATVSNDLKA FTEGAVLSFH NICYRVKLKS
GFLPCRKPVE KEILSNINGI MKPGLNAILG PTGGGKSSLL DVLAARKDPS
GLSGDVLING APRPANFKCN SGYVVQDDVV MGTLTVRENL QFSAALRLAT
TMTNHEKNER INRVIEELGL DKVADSKVGT QFIRGVSGGE RKRTSIGMEL
ITDPSILSLD EPTTGLDSST ANAVLLLLKR MSKQGRTIIF SIHQPRYSIF KLFDSLTLLA
SGRLMFHGPA QEALGYFESA GYHCEAYNNP ADFFLDIING DSTAVALNRE
EDFKATEIIE PSKQDKPLIE KLAEIYVNSS FYKETKAELH QLSGGEKKKK
ITVFKEISYT TSFCHQLRWV SKRSFKNLLG NPQASIAQII VTVVLGLVIG
AIYFGLKNDS TGIQNRAGVL FFLTTNQCFS SVSAVELFVV EKKLFIHEYI
SGYYRVSSYF LGKLLSDLLP MRMLPSIIFT CIVYFMLGLK PKADAFFVMM
FTLMMVAYSA SSMALAIAAG QSVVSVATLL MTICFVFMMI FSGLLVNLTT
IASWLSWLQY FSIPRYGFTA LQHNEFLGQN FCPGLNATGN NPCNYATCTG
EEYLVKQGID LSPWGLWKNH VALACMIVIF LTIAYLKLLF LKKYS

Figure 2

SEQUENCE LISTING

```
<160> NUMBER OF SEQ ID NOS: 65

<210> SEQ ID NO 1
<211> LENGTH: 24
<212> TYPE: PRT
<213> ORGANISM: Artificial Sequence
<220> FEATURE:
<223> OTHER INFORMATION: ABC transporter protein MDR1 inhibiting peptide
      TM1 analog

<400> SEQUENCE: 1

Val Gly Thr Leu Ala Ala Ile Ile His Gly Ala Gly Leu Pro Leu Met
 1               5                  10                  15

Met Leu Val Phe Gly Glu Asp Asp
            20
```

```
<210> SEQ ID NO 2
<211> LENGTH: 23
<212> TYPE: PRT
<213> ORGANISM: Artificial Sequence
<220> FEATURE:
<223> OTHER INFORMATION: ABC transporter protein MDR1 inhibiting peptide
      TM2 analog

<400> SEQUENCE: 2

Asp Asp Tyr Ala Tyr Tyr Tyr Ser Gly Ile Gly Ala Gly Val Leu Val
1               5                   10                  15

Ala Ala Tyr Ile Gln Val Ser
            20

<210> SEQ ID NO 3
<211> LENGTH: 23
<212> TYPE: PRT
<213> ORGANISM: Artificial Sequence
<220> FEATURE:
<223> OTHER INFORMATION: ABC transporter protein MDR1 inhibiting peptide
      TM3 analog

<400> SEQUENCE: 3

Ile Gly Met Phe Phe Gln Ser Met Ala Thr Phe Phe Thr Gly Phe Ile
1               5                   10                  15

Val Gly Phe Thr Gly Gly Asp
            20

<210> SEQ ID NO 4
<211> LENGTH: 23
<212> TYPE: PRT
<213> ORGANISM: Artificial Sequence
<220> FEATURE:
<223> OTHER INFORMATION: ABC transporter protein MDR1 inhibiting peptide
      TM4 analog

<400> SEQUENCE: 4

Ser Ser Asp Asp Thr Leu Thr Leu Val Ile Leu Ala Ile Ser Pro Val
1               5                   10                  15

Leu Gly Leu Ser Ala Ala Val
            20

<210> SEQ ID NO 5
<211> LENGTH: 26
<212> TYPE: PRT
<213> ORGANISM: Artificial Sequence
<220> FEATURE:
<223> OTHER INFORMATION: ABC transporter protein MDR1 inhibiting peptide
      TM5 analog 2

<400> SEQUENCE: 5

Leu Leu Ile Tyr Ala Ser Tyr Ala Leu Ala Phe Trp Tyr Gly Thr Thr
1               5                   10                  15

Leu Val Leu Ser Gly Glu Gly Ser Ser Gly
            20                  25

<210> SEQ ID NO 6
<211> LENGTH: 24
<212> TYPE: PRT
<213> ORGANISM: Artificial Sequence
<220> FEATURE:
<223> OTHER INFORMATION: ABC transporter protein MDR1 inhibiting peptide
      TM6 analog 1

<400> SEQUENCE: 6
```

-continued

```
Asp Ser Gly Glu Tyr Ser Ile Gly Gln Val Leu Thr Val Phe Phe Ser
1               5                   10                  15

Val Leu Ile Gly Ala Phe Ser Val
            20

<210> SEQ ID NO 7
<211> LENGTH: 22
<212> TYPE: PRT
<213> ORGANISM: Artificial Sequence
<220> FEATURE:
<223> OTHER INFORMATION: ABC transporter protein MDR1 inhibiting peptide
      TM7 analog

<400> SEQUENCE: 7

Ala Ile Ile Asn Gly Gly Leu Gln Pro Ala Phe Ala Ile Ile Phe Ser
1               5                   10                  15

Lys Ile Ile Gly Asp Asp
            20

<210> SEQ ID NO 8
<211> LENGTH: 21
<212> TYPE: PRT
<213> ORGANISM: Artificial Sequence
<220> FEATURE:
<223> OTHER INFORMATION: ABC transporter protein MDR1 inhibiting peptide
      TM8 analog

<400> SEQUENCE: 8

Gly Asp Asp Ser Leu Phe Ser Leu Leu Phe Leu Ala Leu Gly Ile Ile
1               5                   10                  15

Ser Phe Ile Thr Phe
            20

<210> SEQ ID NO 9
<211> LENGTH: 24
<212> TYPE: PRT
<213> ORGANISM: Artificial Sequence
<220> FEATURE:
<223> OTHER INFORMATION: ABC transporter protein MDR1 inhibiting peptide
      TM9 analog

<400> SEQUENCE: 9

Leu Ala Val Ile Thr Gln Asn Ile Ala Asn Leu Gly Thr Gly Ile Ile
1               5                   10                  15

Ile Ser Phe Ile Tyr Gly Asp Asp
            20

<210> SEQ ID NO 10
<211> LENGTH: 19
<212> TYPE: PRT
<213> ORGANISM: Artificial Sequence
<220> FEATURE:
<223> OTHER INFORMATION: ABC transporter protein MDR1 inhibiting peptide
      TM10 analog

<400> SEQUENCE: 10

Gly Asp Asp Gly Trp Gln Leu Thr Leu Leu Leu Leu Ala Ile Val Pro
1               5                   10                  15

Ile Ile Ala

<210> SEQ ID NO 11
<211> LENGTH: 23
<212> TYPE: PRT
<213> ORGANISM: Artificial Sequence
```

```
<220> FEATURE:
<223> OTHER INFORMATION: ABC transporter protein MDR1 inhibiting peptide
      TM11 analog

<400> SEQUENCE: 11

Ile Phe Gly Ile Thr Phe Ser Phe Thr Gln Ala Met Met Tyr Phe Ser
1               5                   10                  15

Tyr Ala Gly Cys Phe Asp Asp
            20

<210> SEQ ID NO 12
<211> LENGTH: 25
<212> TYPE: PRT
<213> ORGANISM: Artificial Sequence
<220> FEATURE:
<223> OTHER INFORMATION: ABC transporter protein MDR1 inhibiting peptide
      TM12 analog

<400> SEQUENCE: 12

Asp Asp Asp Leu Met Ser Phe Glu Asp Val Leu Leu Val Phe Ser Ala
1               5                   10                  15

Val Val Phe Gly Ala Met Ala Val Gly
            20                  25

<210> SEQ ID NO 13
<211> LENGTH: 23
<212> TYPE: PRT
<213> ORGANISM: Artificial Sequence
<220> FEATURE:
<223> OTHER INFORMATION: ABC transporter protein BCRP/MXR/ABCP
      inhibiting peptide TM1 analog

<400> SEQUENCE: 13

Ile Ile Val Thr Val Val Leu Gly Leu Val Ile Gly Ala Ile Tyr Phe
1               5                   10                  15

Gly Leu Lys Asn Asp Ser Asp
            20

<210> SEQ ID NO 14
<211> LENGTH: 25
<212> TYPE: PRT
<213> ORGANISM: Artificial Sequence
<220> FEATURE:
<223> OTHER INFORMATION: ABC transporter protein BCRP/MXR/ABCP
      inhibiting peptide TM2 analog

<400> SEQUENCE: 14

Asp Ala Gly Val Leu Phe Phe Leu Thr Thr Asn Gln Cys Phe Ser Ser
1               5                   10                  15

Val Ser Ala Val Glu Leu Phe Val Val
            20                  25

<210> SEQ ID NO 15
<211> LENGTH: 26
<212> TYPE: PRT
<213> ORGANISM: Artificial Sequence
<220> FEATURE:
<223> OTHER INFORMATION: ABC transporter protein BCRP/MXR/ABCP
      inhibiting peptide TM3 analog

<400> SEQUENCE: 15

Leu Leu Pro Met Arg Met Leu Pro Ser Ile Ile Phe Thr Cys Ile Val
1               5                   10                  15

Tyr Phe Met Leu Gly Leu Lys Pro Asp Asp
            20                  25
```

```
<210> SEQ ID NO 16
<211> LENGTH: 25
<212> TYPE: PRT
<213> ORGANISM: Artificial Sequence
<220> FEATURE:
<223> OTHER INFORMATION: ABC transporter protein BCRP/MXR/ABCP
      inhibiting peptide TM4 analog

<400> SEQUENCE: 16

Asp Asp Ala Phe Phe Val Met Met Phe Thr Leu Met Met Val Ala Tyr
 1               5                  10                  15

Ser Ala Ser Ser Met Ala Leu Ala Ile
            20                  25

<210> SEQ ID NO 17
<211> LENGTH: 22
<212> TYPE: PRT
<213> ORGANISM: Artificial Sequence
<220> FEATURE:
<223> OTHER INFORMATION: ABC transporter protein BCRP/MXR/ABCP
      inhibiting peptide TM5 analog

<400> SEQUENCE: 17

Leu Leu Met Thr Ile Cys Phe Val Phe Met Met Ile Phe Ser Gly Leu
 1               5                  10                  15

Leu Val Asn Leu Asp Asp
            20

<210> SEQ ID NO 18
<211> LENGTH: 24
<212> TYPE: PRT
<213> ORGANISM: Artificial Sequence
<220> FEATURE:
<223> OTHER INFORMATION: ABC transporter protein BCRP/MXR/ABCP
      inhibiting peptide TM6 analog

<400> SEQUENCE: 18

Asp Asp Asn His Val Ala Leu Ala Cys Met Ile Val Ile Phe Leu Thr
 1               5                  10                  15

Ile Ala Tyr Leu Lys Leu Leu Phe
            20

<210> SEQ ID NO 19
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM1 analog

<400> SEQUENCE: 19

Gly Ile Phe Leu Ala Pro Val Phe Leu Val Ser Pro Thr Leu Leu Gly
 1               5                  10                  15

Ile Thr Thr Ile Asp Asp
            20

<210> SEQ ID NO 20
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM2 analog

<400> SEQUENCE: 20
```

-continued

Asp Asp Ser Ser Gly Ile Met Leu Thr Phe Trp Leu Val Ala Leu Val
1               5                   10                  15

Cys Ala Leu Ala Ile Leu
            20

<210> SEQ ID NO 21
<211> LENGTH: 25
<212> TYPE: PRT
<213> ORGANISM: Artificial Sequence
<220> FEATURE:
<223> OTHER INFORMATION: ABC transporter protein MRP1 inhibiting
      peptide TM3 analog

<400> SEQUENCE: 21

Phe Tyr Val Tyr Phe Ser Leu Leu Leu Ile Gln Leu Val Leu Ser Cys
1               5                   10                  15

Phe Ser Asp Arg Ser Pro Leu Asp Asp
            20                  25

<210> SEQ ID NO 22
<211> LENGTH: 21
<212> TYPE: PRT
<213> ORGANISM: Artificial Sequence
<220> FEATURE:
<223> OTHER INFORMATION: ABC transporter protein MRP1 inhibiting
      peptide TM4 analog

<400> SEQUENCE: 22

Asp Asp Gly Tyr Phe Tyr Thr Val Leu Leu Phe Val Thr Ala Cys Leu
1               5                   10                  15

Gln Thr Leu Val Leu
            20

<210> SEQ ID NO 23
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM5 analog

<400> SEQUENCE: 23

Ile Asn Met Ile Trp Ser Ala Pro Leu Gln Val Ile Leu Ala Leu Tyr
1               5                   10                  15

Leu Leu Trp Leu Asp Asp
            20

<210> SEQ ID NO 24
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM6 analog

<400> SEQUENCE: 24

Asp Asp Gly Pro Ser Val Leu Ala Gly Val Ala Val Met Val Leu Met
1               5                   10                  15

Val Pro Val Asn Ala Val
            20

<210> SEQ ID NO 25
<211> LENGTH: 23
<212> TYPE: PRT

```
<213> ORGANISM: Artificial Sequence
<220> FEATURE:
<223> OTHER INFORMATION: ABC transporter protein MRP1 inhibiting
      peptide TM7 analog

<400> SEQUENCE: 25

Thr Pro Phe Leu Val Ala Leu Cys Thr Phe Ala Val Tyr Val Thr Ile
 1               5                  10                  15

Asp Glu Asn Asn Ile Leu Asp
            20

<210> SEQ ID NO 26
<211> LENGTH: 21
<212> TYPE: PRT
<213> ORGANISM: Artificial Sequence
<220> FEATURE:
<223> OTHER INFORMATION: ABC transporter protein MRP1 inhibiting
      peptide TM8 analog

<400> SEQUENCE: 26

Asp Asp Phe Asn Ile Leu Arg Phe Pro Leu Asn Ile Leu Pro Met Val
 1               5                  10                  15

Ile Ser Ser Ile Val
            20

<210> SEQ ID NO 27
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM9 analog

<400> SEQUENCE: 27

Ala Ile Gly Leu Phe Ile Ser Phe Leu Ser Ile Phe Leu Phe Met Cys
 1               5                  10                  15

Asn His Val Ser Asp Asp
            20

<210> SEQ ID NO 28
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM10 analog

<400> SEQUENCE: 28

Asp Asp Ser Gln Gly Ile Ala Val Phe Gly Tyr Ser Met Ala Val Ser
 1               5                  10                  15

Ile Gly Gly Ile Leu Ala
            20

<210> SEQ ID NO 29
<211> LENGTH: 22
<212> TYPE: PRT
<213> ORGANISM: Artificial Sequence
<220> FEATURE:
<223> OTHER INFORMATION: ABC transporter protein MRP1 inhibiting
      peptide TM11 analog

<400> SEQUENCE: 29

Val Ile Gly Ala Cys Ile Val Ile Leu Leu Ala Thr Pro Ile Ala Ala
 1               5                  10                  15

Ile Ile Ile Pro Asp Asp
```

<210> SEQ ID NO 30
<211> LENGTH: 20
<212> TYPE: PRT
<213> ORGANISM: Artificial Sequence
<220> FEATURE:
<223> OTHER INFORMATION: ABC transporter protein MRP1 inhibiting peptide TM12 analog

<400> SEQUENCE: 30

Asp Asp Glu Cys Val Gly Asn Cys Ile Val Leu Phe Ala Ala Leu Phe
1               5                   10                  15

Ala Val Ile Ser
            20

<210> SEQ ID NO 31
<211> LENGTH: 23
<212> TYPE: PRT
<213> ORGANISM: Artificial Sequence
<220> FEATURE:
<223> OTHER INFORMATION: ABC transporter protein MRP2 inhibiting peptide TM1 analog

<400> SEQUENCE: 31

Val Leu Val Trp Ile Pro Leu Gly Phe Leu Trp Leu Leu Ala Pro Trp
1               5                   10                  15

Gln Leu Leu His Val Asp Asp
            20

<210> SEQ ID NO 32
<211> LENGTH: 22
<212> TYPE: PRT
<213> ORGANISM: Artificial Sequence
<220> FEATURE:
<223> OTHER INFORMATION: ABC transporter protein MRP2 inhibiting peptide TM2 analog

<400> SEQUENCE: 32

Asp Asp Gln Val Phe Val Gly Phe Leu Leu Ile Leu Ala Ala Ile Glu
1               5                   10                  15

Leu Ala Leu Val Leu Thr
            20

<210> SEQ ID NO 33
<211> LENGTH: 23
<212> TYPE: PRT
<213> ORGANISM: Artificial Sequence
<220> FEATURE:
<223> OTHER INFORMATION: ABC transporter protein MRP2 inhibiting peptide TM3 analog

<400> SEQUENCE: 33

Pro Ala Val Arg Tyr Thr Asn Pro Ser Leu Tyr Leu Gly Thr Trp Leu
1               5                   10                  15

Leu Val Leu Leu Ile Asp Asp
            20

<210> SEQ ID NO 34
<211> LENGTH: 23
<212> TYPE: PRT
<213> ORGANISM: Artificial Sequence
<220> FEATURE:
<223> OTHER INFORMATION: ABC transporter protein MRP2 inhibiting peptide TM4 analog

```
<400> SEQUENCE: 34

Asp Asp Phe Leu Ser Leu Phe Trp Ile Leu Ser Ile Leu Cys Gly Thr
1               5                   10                  15

Phe Gln Phe Gln Thr Leu Ile
            20

<210> SEQ ID NO 35
<211> LENGTH: 27
<212> TYPE: PRT
<213> ORGANISM: Artificial Sequence
<220> FEATURE:
<223> OTHER INFORMATION: ABC transporter protein MRP2 inhibiting
      peptide TM5 analog

<400> SEQUENCE: 35

Asn Leu Ala Tyr Ser Cys Leu Phe Phe Ile Ser Tyr Gly Phe Gln Ile
1               5                   10                  15

Leu Ile Leu Ile Phe Ser Ala Phe Ser Glu Asp
            20                  25

<210> SEQ ID NO 36
<211> LENGTH: 25
<212> TYPE: PRT
<213> ORGANISM: Artificial Sequence
<220> FEATURE:
<223> OTHER INFORMATION: ABC transporter protein MRP2 inhibiting
      peptide TM6 analog

<400> SEQUENCE: 36

Asp Asp Lys Thr Phe Tyr Met Val Leu Leu Lys Ser Phe Leu Leu Lys
1               5                   10                  15

Leu Val Asn Asp Ile Phe Thr Phe Val
            20                  25

<210> SEQ ID NO 37
<211> LENGTH: 24
<212> TYPE: PRT
<213> ORGANISM: Artificial Sequence
<220> FEATURE:
<223> OTHER INFORMATION: ABC transporter protein MRP2 inhibiting
      peptide TM7 analog

<400> SEQUENCE: 37

Thr Tyr Leu Trp Ile Gly Tyr Leu Cys Ala Ile Leu Leu Phe Thr Ala
1               5                   10                  15

Ala Leu Ile Gln Ser Phe Asp Asp
            20

<210> SEQ ID NO 38
<211> LENGTH: 24
<212> TYPE: PRT
<213> ORGANISM: Artificial Sequence
<220> FEATURE:
<223> OTHER INFORMATION: ABC transporter protein MRP2 inhibiting
      peptide TM8 analog

<400> SEQUENCE: 38

Asp Asp Thr Asn Phe Met His Met Leu Trp Ser Ser Val Leu Gln Ile
1               5                   10                  15

Val Leu Ser Ile Phe Phe Leu Trp
            20

<210> SEQ ID NO 39
<211> LENGTH: 24
```

```
<212> TYPE: PRT
<213> ORGANISM: Artificial Sequence
<220> FEATURE:
<223> OTHER INFORMATION: ABC transporter protein MRP2 inhibiting
      peptide TM9 analog

<400> SEQUENCE: 39

Leu Gly Pro Ser Val Leu Ala Gly Val Gly Val Met Val Leu Val Ile
1               5                   10                  15

Pro Ile Asn Ala Ile Leu Asp Asp
            20

<210> SEQ ID NO 40
<211> LENGTH: 26
<212> TYPE: PRT
<213> ORGANISM: Artificial Sequence
<220> FEATURE:
<223> OTHER INFORMATION: ABC transporter protein MRP2 inhibiting
      peptide TM10 analog

<400> SEQUENCE: 40

Asp Asp Gln Leu Gln Cys Val Val Ile Phe Val Phe Gln Leu Thr Pro
1               5                   10                  15

Val Leu Val Ser Val Val Thr Phe Ser Val
            20                  25

<210> SEQ ID NO 41
<211> LENGTH: 23
<212> TYPE: PRT
<213> ORGANISM: Artificial Sequence
<220> FEATURE:
<223> OTHER INFORMATION: ABC transporter protein MRP2 inhibiting
      peptide TM11 analog

<400> SEQUENCE: 41

Phe Thr Ser Ile Thr Leu Phe Asn Ile Leu Arg Phe Pro Leu Ser Met
1               5                   10                  15

Leu Pro Met Met Ile Asp Asp
            20

<210> SEQ ID NO 42
<211> LENGTH: 25
<212> TYPE: PRT
<213> ORGANISM: Artificial Sequence
<220> FEATURE:
<223> OTHER INFORMATION: ABC transporter protein MRP2 inhibiting
      peptide TM12 analog

<400> SEQUENCE: 42

Asp Asp Gln Ala Ile Gly Leu Phe Ser Ile Phe Phe Ile Ile Leu Ala
1               5                   10                  15

Phe Val Met Asn Ser Val Ala Phe Ile
            20                  25

<210> SEQ ID NO 43
<211> LENGTH: 23
<212> TYPE: PRT
<213> ORGANISM: Artificial Sequence
<220> FEATURE:
<223> OTHER INFORMATION: ABC transporter protein MRP2 inhibiting
      peptide TM13 analog

<400> SEQUENCE: 43

Leu Gly Leu Ala Gln Gly Ile Phe Val Phe Ile Ala His Phe Trp Ser
1               5                   10                  15
```

Ala Phe Gly Phe Val Asp Asp
            20

<210> SEQ ID NO 44
<211> LENGTH: 23
<212> TYPE: PRT
<213> ORGANISM: Artificial Sequence
<220> FEATURE:
<223> OTHER INFORMATION: ABC transporter protein MRP2 inhibiting
      peptide TM14 analog

<400> SEQUENCE: 44

Asp Asp Ser Thr Leu Val Met Ile Cys Met Ala Thr Pro Val Phe Thr
1               5                   10                  15

Ile Ile Val Ile Pro Leu Gly
            20

<210> SEQ ID NO 45
<211> LENGTH: 23
<212> TYPE: PRT
<213> ORGANISM: Artificial Sequence
<220> FEATURE:
<223> OTHER INFORMATION: ABC transporter protein MRP2 inhibiting
      peptide TM15 analog

<400> SEQUENCE: 45

Ala Ile Arg Leu Glu Leu Val Gly Asn Leu Thr Val Phe Phe Ser Ala
1               5                   10                  15

Leu Met Met Val Ile Asp Asp
            20

<210> SEQ ID NO 46
<211> LENGTH: 22
<212> TYPE: PRT
<213> ORGANISM: Artificial Sequence
<220> FEATURE:
<223> OTHER INFORMATION: ABC transporter protein MRP2 inhibiting
      peptide TM16 analog

<400> SEQUENCE: 46

Asp Asp Ser Ser Leu Thr Asn Cys Leu Phe Arg Ile Leu Glu Ala Ala
1               5                   10                  15

Gly Gly Gln Ile Ile Ile
            20

<210> SEQ ID NO 47
<211> LENGTH: 78
<212> TYPE: DNA
<213> ORGANISM: Artificial Sequence
<220> FEATURE:
<223> OTHER INFORMATION: DNA sequence encoding preferred ABC transporter
      protein MDR1 inhibiting peptide TM5 analog

<400> SEQUENCE: 47
cttcttatct acgcgagcta tgcgctcgcc ttctggtatg gtactactct tgtgctttct    60
ggtgagggtt cttctggt                                                  78

<210> SEQ ID NO 48
<211> LENGTH: 1280
<212> TYPE: PRT
<213> ORGANISM: Homo sapiens
<220> FEATURE:
<223> OTHER INFORMATION: human P-glycoprotein 1 (P-gp),
      multidrug resistance protein 1 (MDR1)

<400> SEQUENCE: 48

-continued

```
Met Asp Leu Glu Gly Asp Arg Asn Gly Gly Ala Lys Lys Asn Phe
 1               5                  10                 15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
         35                  40                  45

Leu Tyr Met Val Val Gly Thr Leu Ala Ala Ile Ile His Gly Ala Gly
 50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
                100                 105                 110

Arg Tyr Ala Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
        130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415
```

-continued

```
Val Gln Ser Gly Gln Thr Val Ala Leu Val Gly Asn Ser Gly Cys Gly
            420                 425                 430
Lys Ser Thr Thr Val Gln Leu Met Gln Arg Leu Tyr Asp Pro Thr Glu
        435                 440                 445
Gly Met Val Ser Val Asp Gly Gln Asp Ile Arg Thr Ile Asn Val Arg
    450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
Met Asp Glu Ile Glu Lys Ala Val Lys Glu Ala Asn Ala Tyr Asp Phe
            500                 505                 510
Ile Met Lys Leu Pro His Lys Phe Asp Thr Leu Val Gly Glu Arg Gly
        515                 520                 525
Ala Gln Leu Ser Gly Gly Gln Lys Gln Arg Ile Ala Ile Ala Arg Ala
    530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
            580                 585                 590
Arg Asn Ala Asp Val Ile Ala Gly Phe Asp Asp Gly Val Ile Val Glu
        595                 600                 605
Lys Gly Asn His Asp Glu Leu Met Lys Glu Lys Gly Ile Tyr Phe Lys
    610                 615                 620
Leu Val Thr Met Gln Thr Ala Gly Asn Glu Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
            660                 665                 670
Arg Gly Ser Gln Ala Gln Asp Arg Lys Leu Ser Thr Lys Glu Ala Leu
        675                 680                 685
Asp Glu Ser Ile Pro Pro Val Ser Phe Trp Arg Ile Met Lys Leu Asn
    690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
            740                 745                 750
Asn Leu Phe Ser Leu Leu Phe Leu Ala Leu Gly Ile Ile Ser Phe Ile
        755                 760                 765
Thr Phe Phe Leu Gln Gly Phe Thr Phe Gly Lys Ala Gly Glu Ile Leu
    770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
            820                 825                 830
Leu Ala Val Ile Thr Gln Asn Ile Ala Asn Leu Gly Thr Gly Ile Ile
```

-continued

```
                835                 840                 845
Ile Ser Phe Ile Tyr Gly Trp Gln Leu Thr Leu Leu Leu Ala Ile
    850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
                900                 905                 910
Glu Gln Lys Phe Glu His Met Tyr Ala Gln Ser Leu Gln Val Pro Tyr
                915                 920                 925
Arg Asn Ser Leu Arg Lys Ala His Ile Phe Gly Ile Thr Phe Ser Phe
930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
                980                 985                 990
Ser Phe Ala Pro Asp Tyr Ala Lys Ala Lys Ile Ser Ala Ala His Ile
                995                 1000                1005
Ile Met Ile Ile Glu Lys Thr Pro Leu Ile Asp Ser Tyr Ser Thr Glu
    1010                1015                1020
Gly Leu Met Pro Asn Thr Leu Glu Gly Asn Val Thr Phe Gly Glu Val
1025                1030                1035                1040
Val Phe Asn Tyr Pro Thr Arg Pro Asp Ile Pro Val Leu Gln Gly Leu
                1045                1050                1055
Ser Leu Glu Val Lys Lys Gly Gln Thr Leu Ala Leu Val Gly Ser Ser
                1060                1065                1070
Gly Cys Gly Lys Ser Thr Val Val Gln Leu Leu Glu Arg Phe Tyr Asp
                1075                1080                1085
Pro Leu Ala Gly Lys Val Leu Leu Asp Gly Lys Glu Ile Lys Arg Leu
                1090                1095                1100
Asn Val Gln Trp Leu Arg Ala His Leu Gly Ile Val Ser Gln Glu Pro
1105                1110                1115                1120
Ile Leu Phe Asp Cys Ser Ile Ala Glu Asn Ile Ala Tyr Gly Asp Asn
                1125                1130                1135
Ser Arg Val Val Ser Gln Glu Glu Ile Val Arg Ala Ala Lys Glu Ala
                1140                1145                1150
Asn Ile His Ala Phe Ile Glu Ser Leu Pro Asn Lys Tyr Ser Thr Lys
                1155                1160                1165
Val Gly Asp Lys Gly Thr Gln Leu Ser Gly Gly Gln Lys Gln Arg Ile
    1170                1175                1180
Ala Ile Ala Arg Ala Leu Val Arg Gln Pro His Ile Leu Leu Leu Asp
1185                1190                1195                1200
Glu Ala Thr Ser Ala Leu Asp Thr Glu Ser Glu Lys Val Val Gln Glu
                1205                1210                1215
Ala Leu Asp Lys Ala Arg Glu Gly Arg Thr Cys Ile Val Ile Ala His
                1220                1225                1230
Arg Leu Ser Thr Ile Gln Asn Ala Asp Leu Ile Val Val Phe Gln Asn
    1235                1240                1245
Gly Arg Val Lys Glu His Gly Thr His Gln Gln Leu Leu Ala Gln Lys
    1250                1255                1260
```

```
Gly Ile Tyr Phe Ser Met Val Ser Val Gln Ala Gly Thr Lys Arg Gln
1265                1270                1275                1280

<210> SEQ ID NO 49
<211> LENGTH: 655
<212> TYPE: PRT
<213> ORGANISM: Homo sapiens
<220> FEATURE:
<223> OTHER INFORMATION: human breast cancer resistance protein
      (BCRP/MXR1/ABCP)

<400> SEQUENCE: 49

Met Ser Ser Ser Asn Val Glu Val Phe Ile Pro Val Ser Gln Gly Asn
1               5                   10                  15

Thr Asn Gly Phe Pro Ala Thr Val Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Glu Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Ser
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
```

```
                    340                 345                 350
Ser Gly Gly Glu Lys Lys Lys Ile Thr Val Phe Lys Glu Ile Ser
            355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 50
<211> LENGTH: 24
<212> TYPE: PRT
<213> ORGANISM: Artificial Sequence
<220> FEATURE:
<223> OTHER INFORMATION: ABC transporter protein MDR1 (P-gp) inhibitory
      peptide TM12 analog

<400> SEQUENCE: 50

Asp Glu Asp Val Leu Leu Val Phe Ser Ala Val Val Phe Gly Ala Met
 1               5                  10                  15

Ala Val Gly Gln Val Ser Ser Phe
            20

<210> SEQ ID NO 51
<211> LENGTH: 25
```

```
<212> TYPE: PRT
<213> ORGANISM: Artificial Sequence
<220> FEATURE:
<223> OTHER INFORMATION: ABC transporter protein MDR1 TM1 (residues
      49-73)

<400> SEQUENCE: 51

Leu Tyr Met Val Val Gly Thr Leu Ala Ala Ile Ile His Gly Ala Gly
1               5                   10                  15

Leu Pro Leu Met Met Leu Val Phe Gly
            20                  25

<210> SEQ ID NO 52
<211> LENGTH: 24
<212> TYPE: PRT
<213> ORGANISM: Artificial Sequence
<220> FEATURE:
<223> OTHER INFORMATION: ABC transporter protein MDR1 TM2 (residues
      117-139)

<400> SEQUENCE: 52

Tyr Tyr Ser Gly Ile Gly Ala Gly Val Leu Val Ala Ala Tyr Ile Gln
1               5                   10                  15

Val Ser Phe Trp Cys Leu Ala Ala
            20

<210> SEQ ID NO 53
<211> LENGTH: 20
<212> TYPE: PRT
<213> ORGANISM: Artificial Sequence
<220> FEATURE:
<223> OTHER INFORMATION: ABC transporter protein MDR1 TM3 (residues
      (190-209)

<400> SEQUENCE: 53

Ile Gly Met Phe Phe Gln Ser Met Ala Thr Phe Phe Thr Gly Phe Ile
1               5                   10                  15

Val Gly Phe Thr
            20

<210> SEQ ID NO 54
<211> LENGTH: 24
<212> TYPE: PRT
<213> ORGANISM: Artificial Sequence
<220> FEATURE:
<223> OTHER INFORMATION: ABC transporter protein MDR1 TM4 (residues
      214-236)

<400> SEQUENCE: 54

Leu Thr Leu Val Ile Leu Ala Ile Ser Pro Val Leu Gly Leu Ser Ala
1               5                   10                  15

Ala Val Trp Ala Lys Ile Leu Ser
            20

<210> SEQ ID NO 55
<211> LENGTH: 27
<212> TYPE: PRT
<213> ORGANISM: Artificial Sequence
<220> FEATURE:
<223> OTHER INFORMATION: ABC transporter protein MDR1 TM5 (residues
      297-323)

<400> SEQUENCE: 55

Ile Ser Ile Gly Ala Ala Phe Leu Leu Ile Tyr Ala Ser Tyr Ala Leu
1               5                   10                  15
```

-continued

Ala Phe Trp Tyr Gly Thr Thr Leu Val Leu Ser
            20                  25

<210> SEQ ID NO 56
<211> LENGTH: 25
<212> TYPE: PRT
<213> ORGANISM: Artificial Sequence
<220> FEATURE:
<223> OTHER INFORMATION: ABC transporter protein MDR1 inhibitory peptide
      TM5 analog 1

<400> SEQUENCE: 56

Ile Ser Ile Gly Ala Ala Phe Leu Leu Ile Tyr Ala Ser Tyr Ala Leu
1               5                   10                  15

Ala Phe Trp Tyr Gly Thr Thr Asp Asp
            20                  25

<210> SEQ ID NO 57
<211> LENGTH: 27
<212> TYPE: PRT
<213> ORGANISM: Artificial Sequence
<220> FEATURE:
<223> OTHER INFORMATION: ABC transporter protein MDR1 TM6 (residues
      326-352)

<400> SEQUENCE: 57

Tyr Ser Ile Gly Gln Val Leu Thr Val Phe Phe Ser Val Leu Ile Gly
1               5                   10                  15

Ala Phe Ser Val Gly Gln Ala Ser Pro Ser Ile
            20                  25

<210> SEQ ID NO 58
<211> LENGTH: 27
<212> TYPE: PRT
<213> ORGANISM: Artificial Sequence
<220> FEATURE:
<223> OTHER INFORMATION: ABC transporter protein MDR1 inhibitory peptide
      TM6 analog 2

<400> SEQUENCE: 58

Asp Asp Gly Ser Gly Glu Tyr Ser Ile Gly Gln Val Leu Thr Val Phe
1               5                   10                  15

Phe Ser Val Leu Ile Gly Ala Phe Ser Val Gly
            20                  25

<210> SEQ ID NO 59
<211> LENGTH: 27
<212> TYPE: PRT
<213> ORGANISM: Artificial Sequence
<220> FEATURE:
<223> OTHER INFORMATION: ABC transporter protein MDR1 inhibitory peptide
      TM6 analog 3

<400> SEQUENCE: 59

Asp Asp Asp Ser Gly Glu Tyr Ser Ile Gly Gln Val Leu Thr Val Phe
1               5                   10                  15

Phe Ser Val Leu Ile Gly Ala Phe Ser Val Gly
            20                  25

<210> SEQ ID NO 60
<211> LENGTH: 29
<212> TYPE: PRT
<213> ORGANISM: Artificial Sequence
<220> FEATURE:
<223> OTHER INFORMATION: ABC transporter protein MDR1 TM7 (residues
      708-728)

```
<400> SEQUENCE: 60

Trp Pro Tyr Phe Val Val Gly Val Phe Cys Ala Ile Ile Asn Gly Gly
1               5                   10                  15

Leu Gln Pro Ala Phe Ala Ile Ile Phe Ser Lys Ile Ile
            20                  25

<210> SEQ ID NO 61
<211> LENGTH: 24
<212> TYPE: PRT
<213> ORGANISM: Artificial Sequence
<220> FEATURE:
<223> OTHER INFORMATION: ABC transporter protein MDR1 TM8 (residues
      754-776)

<400> SEQUENCE: 61

Leu Phe Ser Leu Leu Phe Leu Ala Leu Gly Ile Ile Ser Phe Ile Thr
1               5                   10                  15

Phe Phe Leu Gln Gly Phe Thr Phe
            20

<210> SEQ ID NO 62
<211> LENGTH: 21
<212> TYPE: PRT
<213> ORGANISM: Artificial Sequence
<220> FEATURE:
<223> OTHER INFORMATION: ABC transporter protein MDR1 TM9 (residues
      833-853)

<400> SEQUENCE: 62

Leu Ala Val Ile Thr Gln Asn Ile Ala Asn Leu Gly Thr Gly Ile Ile
1               5                   10                  15

Ile Ser Phe Ile Tyr
            20

<210> SEQ ID NO 63
<211> LENGTH: 21
<212> TYPE: PRT
<213> ORGANISM: Artificial Sequence
<220> FEATURE:
<223> OTHER INFORMATION: ABC transporter protein MDR1 TM10 (residues
      854-874)

<400> SEQUENCE: 63

Gly Trp Gln Leu Thr Leu Leu Leu Leu Ala Ile Val Pro Ile Ile Ala
1               5                   10                  15

Ile Ala Gly Val Val
            20

<210> SEQ ID NO 64
<211> LENGTH: 21
<212> TYPE: PRT
<213> ORGANISM: Artificial Sequence
<220> FEATURE:
<223> OTHER INFORMATION: ABC transporter protein MDR1 TM11 (residues
      937-957)

<400> SEQUENCE: 64

Ile Phe Gly Ile Thr Phe Ser Phe Thr Gln Ala Met Met Tyr Phe Ser
1               5                   10                  15

Tyr Ala Gly Cys Phe
            20

<210> SEQ ID NO 65
```

-continued

```
<211> LENGTH: 22
<212> TYPE: PRT
<213> ORGANISM: Artificial Sequence
<220> FEATURE:
<223> OTHER INFORMATION: ABC transporter protein MDR1 TM12 (residues
      974-995)

<400> SEQUENCE: 65

Val Leu Leu Val Phe Ser Ala Val Val Phe Gly Ala Met Ala Val Gly
1               5                   10                  15

Gln Val Ser Ser Phe Ala
            20
```

INHIBITION OF ABC TRANSPORTERS BY TRANSMEMBRANE DOMAIN ANALOGS

CROSS-REFERENCES TO RELATED APPLICATIONS

This case is a continuation in part of U.S. Provisional Application No. 60/166,382, filed Nov. 18, 1999, and of U.S. Provisional Application No. 60/166,767, filed Nov. 22, 1999. The contents of both applications are incorporated herein by reference.

STATEMENT REGARDING FEDERALLY SPONSORED RESEARCH

Not applicable.

FIELD OF THE INVENTION

The present invention relates to inhibiting, the biological activities of ATP-binding cassette ("ABC") transporters by exposing the ABC transporters to molecules which interfere with correct transporter assembly. In particular, the invention relates to synthetic, isolated and/or recombinant peptides, fragments and/or consensus peptides of one or more transmembrane domains of ABC transporters that inhibit ABC transporter-mediated transport.

BACKGROUND OF THE INVENTION

ATP-binding cassette ("ABC") transporters play a role in the transport of a multitude of substrates in the body (for a review of ABC transporters, see Holland, B. and Blight, M., *J. Mol. Biol.* 293:381-399 (1999). For example, the human MDR1 gene encodes an ABC transporter, P-glycoprotein ("P-gp"), that mediates multiple drug resistance ("MDR") to a number of antitumor agents (reviewed in Ambudkar, S. V. et al., *Ann. Rev. Pharmacol. Toxicol.* 39:361-98 (1999)). The protein is clinically important because it confers multidrug resistance to cancer cells, and interferes in the treatment of AIDS by inhibiting oral absorption and brain entry of HIV-1 protease inhibitors. (Wacher V. J. et al., *J Pharm Sci.* 87:1322-30 (1998)). P-gp functions as an ATP-dependent efflux pump that transports drugs out of the cells.

Human P-gp, encoded by the MDR1 gene, consists of 1280 amino acids organized in two tandem repeats of 610 amino acids, joined by a linker region of 60 amino acids. Each repeat consists of an $NH_2$-terminal hydrophobic domain containing six potential transmembrane ("TM") sequences followed by a hydrophilic domain containing a nucleotide-binding site. (Chen, C. J. et al., *Cell* 47:381-389 (1986)). The amino acid sequence and domain organization of the protein is typical of the ABC superfamily of transporters. (Higgins, C. F. *Annu Rev. Cell Biol* 8:67-113 (1992)).

Transmembrane domains of P-gp were demonstrated to be directly involved in binding of the substrates. (Zhang, X. et al., *J. Biol Chem,* 270:5441-8 (1995); Demeule M. et al.; *Biochemistry* 37:18110-8 (1998); Wu Q, et al, *Biochemistry,* 37:11272-9 (1998)). Intramembrane interaction within P-gp have been suggested to be crucial for superfolding and assembly of the protein molecule. (Loo T. W. et al.; *J. Biol. Chem.,* 273:14671-4 (1998)).

SUMMARY OF THE INVENTION

The invention provides isolated ATP-binding cassette (ABC) transporter protein-inhibiting peptide, wherein said peptide has a first end and a second end, and said peptide has at said first end a group that is negatively charged under physiological conditions and at said second end has a group that is neutrally charged under physiological conditions; said first end comprises 1 to 6 amino acid residues, of which at least 1 is negatively charged at physiological pH; said second end has at least 70% sequence identity to a transmembrane domain of an ABC transporter protein; said peptide spontaneously inserts into a membrane in the same orientation as the ABC transporter transmembrane domain with which it shares sequence identity; and said peptide inhibits a biological property or activity of said ABC transporter. In some embodiments, the negatively charged group at the first end of the peptide is comprised of one to three amino acid residues that are negatively charged under physiological conditions. The negative charge of the group at the first end of the peptide can be provided, for example, by a carboxyl, phosphate, borate, sulfonate or sulfate functional group.

The ABC transporter can be, for example, MDR1, MRP1, MDR3, BCRP/MXR/ABCP, MXR2, MRP2/cMOAT/ABCC2, MOAT-B, MOAT-D, ABC1, pABC11, MOAT-E, ABCR, ABCB3, ABCG1, ABCG2, ABCB7, ABCA3, Bcrp, mdr1, mdr3, human peroxisomal ABC-transporter (as encoded by GenBank Accession No. NM_005050), CgCDR1, Pdr12, *S. typhimurium* oxd-6, *N. meningitidis* abcZ, an expression product encoded by *Y. enterocolitica* enterochelin/enterobactin gene cluster, and an expression product encoded by a *M. agalactiae* P48 gene. In one set of embodiments, the ABC transporter is MDR1, and the peptide has a sequence selected from the group of sequences consisting of: VGTLAAIIHGAGLPLMMLVFGEDD (SEQ ID NO:1); DDYAYYYSGIGAGVLVAAYIQVS (SEQ ID NO:2); IGMFFQSMATFFTGFIVGFTGGD (SEQ ID NO:3); SSDDTLTLVILAISPVLGLSAAV (SEQ ID NO:4); LLIYASYALAFWYGTTLVLSGEGSSG (SEQ ID NO:5); DSGEYSIGQVLTVFFSVLIGAFSV (SEQ ID NO:6); AIINGGLQPAFAIIFSKIIGDD (SEQ ID NO:7); GDDSLF-SLLFLALGIISFITF (SEQ ID NO:8); LAVITQNIANLGT-GIIISFIYGDD (SEQ ID NO:9); GDDG-WQLTLLLLAIVPIIA (SEQ ID NO:10); IFGITFSFTQAMMYFSYAGCFDD (SEQ ID NO:11); and, DDDLMSFEDVLLVFSAVVFGAMAVG (SEQ ID NO:12). In a particularly preferred embodiment, the peptide is LLI-YASYALAFWYGTTLVLSGEGSSG (SEQ ID NO:5). The biological activity of MDR1 modulated by the peptide is preferably efflux of a cytotoxin from cytoplasm of a cell expressing MDR1. In preferred embodiments, the cytotoxin whose efflux is modulated by the peptide is selected from the group consisting of topotecan, mitoxantrone, doxorubicin, daunorubicin, etoposide, vincristine, and vinblastine.

In another group of embodiments, the ABC transporter is the Breast Cancer Resistance Protein (BCRP), and the peptide has a sequence selected from the group of sequences consisting of: IIVTVVLGLVIGAIYFGLKNDSD (SEQ ID NO:13); DAGVLFFLTTNQCFSSVSAVELFVV (SEQ ID NO:14); LLPMRMLPSIIFTCIVYFMLGLKPDD (SEQ ID NO:15); DDAFFVMMFTLMMVAYSASSMALAI (SEQ ID NO:16); LLMTICFVFMMIFSGLLVNLDD (SEQ ID NO:17); and DDNHVALACMIVIFLTIAYLKLLF (SEQ ID NO:18) and wherein the peptide molecule inhibits a biological activity of BCRP. In some embodiments the biological activity of BCRP inhibited by the peptide is efflux of a chemotherapeutic agent from cytoplasm of a cell expressing BCRP. In preferred embodiments, the chemotherapeutic agent whose efflux is modulated by the peptide is selected from the group consisting of topotecan, mitoxantrone, doxorubicin, daunorubicin, etoposide, vincristine, and vinblastine.

In yet another group of embodiments, the ABC transporter is MRP1 and the peptide has a sequence selected from the group of sequences consisting of: GIFLAPVFLVSPTLLGITTIDD (SEQ ID NO:19); DDSSGIMLTFWLVALVCALAIL (SEQ ID NO:20); FYVYFSLLLIQLVLSCFSDRSPLDD (SEQ ID NO:21); DDGYFYTVLLFVTACLQTLVL (SEQ ID NO:22); INMIWSAPLQVILALYLLWLDD (SEQ ID NO:23); DDGPSVLAGVAVMVLMVPVNAV (SEQ ID NO:24); TPFLVALCTFAVYVTIDENNILD (SEQ ID NO:25); DDFNILRFPLNILPMVISSIV (SEQ ID NO:26); AIGLFISFLSIFLFMCNHVSDD (SEQ ID NO:27); DDSQGIAVFGYSMAVSIGGILA (SEQ ID NO:28); VIGACIVILLATPIAAIIIPDD (SEQ ID NO:29); and DDECVGNCIVLFAALFAVIS (SEQ ID NO:30); and wherein the peptide inhibits a biological activity of MRP1. In some embodiments, the biological activity of MRP1 inhibited by the peptide is efflux of a chemotherapeutic agent from cytoplasm of a cell expressing MRP1. In preferred embodiments, the chemotherapeutic agent whose efflux is modulated by the peptide is selected from the group consisting of topotecan, mitoxantrone, doxorubicin, daunorubicin, etoposide, vincristine, and vinblastine.

In yet a further group of embodiments, the invention concerns embodiments wherein the ABC transporter is MRP2, and the peptide has a sequence selected from the group of sequences consisting of: VLVWIPLGFLWLLAPWQLLHVDD (SEQ ID NO:31); DDQVFVGFLLILAAIELALVLT (SEQ ID NO:32); PAVRYTNPSLYLGTWLLVLLIDD (SEQ ID NO:33); DDFLSLFWILSILCGTFQFQTLI (SEQ ID NO:34); NLAYSCLFFISYGFQILILIFSAFSED (SEQ ID NO:35); DDKTFYMVLLKSFLLKLVNDIFTFV (SEQ ID NO:36); TYLWIGYLCAILLFTAALIQSFDD (SEQ ID NO:37); DDTNFMHMLWSSVLQIVLSIFFLW (SEQ ID NO:38); LGPSVLAGVGVMVLVIPINAILDD (SEQ ID NO:39); DDQLQCVVIFVFQLTPVLVSVVTFSV (SEQ ID NO:40); FTSITLFNILRFPLSMLPMMIDD (SEQ ID NO:41); DDQAIGLFSIFFIILAFVMNSVAFI (SEQ ID NO:42); LGLAQGIFVFIAHFWSAFGFVDD (SEQ ID NO:43); DDSTLVMICMATPVFTIIVIPLG (SEQ ID NO:44); AIRLELVGNLTVFFSALMMVIDD (SEQ ID NO:45); and DDSSLTNCLFRILEAAGGQIII (SEQ ID NO:46) and wherein said peptide inhibits a biological activity of MRP2. In some embodiments, the biological activity of MRP2 inhibited by said peptide is efflux of a chemotherapeutic agent from cytoplasm of a cell expressing MRP2. In preferred embodiments, the chemotherapeutic agent whose efflux is modulated by said peptide is selected from the group consisting of topotecan, mitoxantrone, doxorubicin, cisplatin, CPT-11, SN-38, and camptothesins.

In another group of embodiments, the invention provides any of the peptides described above in a pharmaceutically acceptable carrier. Further, the invention provides a method of inhibiting the biological activity of a target ATP-binding cassette ("ABC") transporter, said method comprising contacting a cell that expresses said ABC transporter with one of the above-described peptides. In preferred embodiments, the peptide is present in a concentration of about 0.01 to about 100 micromolar. The inhibited biological activity is selected from the group consisting of ion flux or translocation, cytotoxin efflux or translocation, phosphorylation, protein synthesis or degradation, cellular morphology, secretion, production of particular components such as soluble inositol phosphates, tumor growth, chemotaxis, mitogenic response, cell growth activation, and secretion. In one group of particularly preferred embodiments, the inhibited biological activity is inhibition of MDR1-, MRP1-, MRP2-, or BCRP-mediated efflux of a chemotherapeutic agent from said cell.

In another group of embodiments, the invention provides isolated nucleic acid molecules encoding an isolated ATP-binding cassette (ABC) transporter-inhibiting peptides, wherein the peptide has a first end and a second end, and said peptide has at said first end a group that is negatively charged under physiological conditions and at said second end has a group that is neutrally charged under physiological conditions; the first end comprises 1 to 6 amino acid residues, of which at least 1 is negatively charged at physiological pH; said second end has at least 70% sequence identity to a transmembrane domain of an ABC transporter protein; the peptide spontaneously inserts into a membrane in the same orientation as the ABC transporter transmembrane domain with which it shares sequence identity; and the peptide inhibits a biological property or activity of said ABC transporter. In preferred embodiments, the isolated nucleic acid encodes a peptide selected from the group consisting of: VGTLAAIIHGAGLPLMMLVFGEDD (SEQ ID NO:1); DDYAYYYSGIGAGVLVAAYIQVS (SEQ ID NO:2); IGMFFQSMATFFTGFIVGFTGGD (SEQ ID NO:3); SSDDTLTLVILAISPVLGLSAAV (SEQ ID NO:4); LLIYASYALAFWYGTTLVLSGEGSSG (SEQ ID NO:5); DSGEYSIGQVLTVFFSVLIGAFSV (SEQ ID NO:6); AIINGGLQPAFAIIFSKIIGDD (SEQ ID NO:7); GDDSLFSLLLFLALGIISFITF (SEQ ID NO:8); LAVITQNIANLGTGIIISFIYGDD (SEQ ID NO:9); GDDGWQLTLLLLAIVPIIA (SEQ ID NO:10); IFGITFSFTQAMMYFSYAGCFDD (SEQ ID NO:11); DDDLMSFEDVLLVFSAVVFGAMAVG (SEQ ID NO:12); IIVTVVLGLVIGAIYFGLKNDSD (SEQ ID NO:13); DAGVLFFLTTNQCFSSVSAVELFVV (SEQ ID NO:14); LLPMRMLPSIIFTCIVYFMLGLKPDD (SEQ ID NO:15); DDAFFVMMFTLMMVAYSASSMALAI (SEQ ID NO:16); LLMTICFVFMMIFSGLLVNLDD (SEQ ID NO:17); DDNHVALACMIVIFLTIAYLKLLF (SEQ ID NO:18); GIFLAPVFLVSPTLLGITTIDD (SEQ ID NO:19); DDSSGIMLTFWLVALVCALAIL (SEQ ID NO:20); FYVYFSLLLIQLVLSC FSDRSPLDD (SEQ ID NO:21); DDGYFYTVLLFVTACLQTLVL (SEQ ID NO:22); INMIWSAPLQVILALYLLWLDD (SEQ ID NO:23); DDGPSVLAGVAVMVLMVPVNAV (SEQ ID NO:24); TPFLVALCTFAVYVTIDENNILD (SEQ ID NO:25); DDFNILRFPLNILPMVISSIV (SEQ ID NO:26); AIGLFISFLSIFLFMCNHVSDD (SEQ ID NO:27); DDSQGIAVFGYSMAVSIGGILA (SEQ ID NO:28); VIGACIVILLATPIAAIIIPDD (SEQ ID NO:29); DDECVGNCIVLFAALFAVIS (SEQ ID NO:30); VLVWIPLGFLWLLAPWQLLHVDD (SEQ ID NO:31); DDQVFVGFLLILAAIELALVLT (SEQ ID NO:32); PAVRYTNPSLYLGTWLLVLLIDD (SEQ ID NO:33); DDFLSLFWILSILCGTFQFQTLI (SEQ ID NO:34); NLAYSCLFFISYGFQILILIFSAFSED (SEQ ID NO:35); DDKTFYMVLLKSFLLKLVNDIFTFV (SEQ ID NO:36); TYLWIGYLCAILLFTAALIQSFDD (SEQ ID NO:37); DDTNFMHMLWSSVLQIVLSIFFLW (SEQ ID NO:38); LGPSVLAGVGVMVLVIPINAILDD (SEQ ID NO:39); DDQLQCVVIFVFQLTPVLVSVVTFSV (SEQ ID NO:40); FTSITLFNILRFPLSMLPMMIDD (SEQ ID NO:41); DDQAIGLFSIFFIILAFVMNSVAFI (SEQ ID NO:42); LGLAQGIFVFIAHFWSAFGFVDD (SEQ ID NO:43); DDSTLVMICMATPVFTIIVIPLG (SEQ ID NO:44); AIRLELVGNLTVFFSALMMVIDD (SEQ ID NO:45); and DDSSLTNCLFRILEAAGGQIII (SEQ ID NO:46). In a particularly preferred embodiment, the isolated nucleic acid encodes the peptide LLIYASYALAFWYGTTLVLS- GEGSSG (SEQ ID NO:5). In an especially preferred embodiment, the isolated nucleic acid is CTT CTT ATC TAC GCG AGC TAT GCG CTC GCC TTC TGG TAT GGT ACT ACT CTT GTG CTT TCT GGT GAG GGT TCT TCT GGT (SEQ ID NO:47).

The invention further provides an expression cassette comprising a promoter operably linked to one of the above-described nucleic acid molecules. Further, the invention provides host cells comprising one of the expression cassettes of the invention.

The invention further provides a method for determining whether a peptide inhibits substrate transport by an ATP-binding cassette (ABC) transporter protein, said method comprising: contacting a first cell comprising an ABC transporter and a second cell with a fluorescent substrate of the ABC transporter for a time sufficient for the cell to internalize a detectable amount of the substrate; contacting the first cell with the peptide but not contacting the second cell with the peptide; fixing the cells with an alcohol; and determining the relative levels of fluorescence of the first and the second cell, whereby a lower level of fluorescence in the first cell relative to the second cell indicates that the peptide inhibits substrate transport by the ABC transporter.

Finally, the invention also provides an integrated system for comparing inhibition of substrate transport by an ABC transporter protein of a cell contacted by a chemical composition to inhibition of substrate transport by an ABC transporter protein of a second cell not contacted by the chemical composition, comprising: an array reader adapted to read levels of fluorescence on an array, operably linked to a digital computer storing a data file of the respective levels of fluorescence of cells contacted with the chemical composition.

BRIEF DESCRIPTION OF THE DRAWINGS

FIG. 1. Amino acid sequence of human P-gp (SEQ ID NO:48) (product of MDR1 gene). Transmembrane domains predicted on the base of hydropathy analysis are underlined. Amino terminus is intracellular.

FIG. 2. Amino acid sequence of BCRP/MXR/ABCP (SEQ ID NO:49). Transmembrane domains predicted on the base of hydropathy analysis are underlined.

DETAILED DESCRIPTION

Introduction (a) Inhibition of Substrate Transport by ABC Transporters

The present invention provides new compositions and methods for inhibiting the transport of substrates by ATP-binding cassette transporter proteins ("ABC transporters" or "transporters") such as MDR1, the ABC transporter responsible for multidrug resistance in many cancer cells. The invention is based in part on the discovery that polypeptides derived from the amino acid sequence of a transmembrane domain ("TM") of a targeted ABC transporter can, when given appropriate polarity, insert into biological membranes, such as the cell membrane, and interfere with the function of the targeted protein, presumably by infiltrating into the ABC transporter and outcompeting the endogenous domain to interfere with the normal assembly of the transmembrane part of the ABC transporter.

The high speed with which the polypeptides (variously referred to herein as "ABC transporter transmembrane polypeptides," "TM analogs" or, most conveniently, "analogs") interfere with targeted ABC transporters suggests that the analogs disrupt already fully assembled and functional ABC transporters, and not merely the assembly of new ABC transporters. They are therefore capable of quickly reducing or blocking transport of substrate by the targeted ABC transporter. These and other observations have shown that targeting intramembrane interactions of ABC transporter transmembrane domains can specifically regulate ABC transporter function. Accordingly, the invention provides powerful new tools for inhibiting or blocking the undesirable effects of particular ABC transporters. For example, the analogs can be used to reduce the resistance to chemotherapeutic agents which is conferred on cancer cells by ABC transporters such as MDR1, MRP1, MRP2, BCRP, and other ABC transporters. Moreover, since HIV-1 protease inhibitors are also effluxed from cells by ABC transporters such as MDR1 (e.g., Lee et al., Biochemistry 37(11):3594-601 (1998), the analogs can reduce the efflux of protease inhibitors from cells, decreasing the amount of the protease inhibitors necessary to suppress HIV-1. Lowering the doses of protease inhibitors needed to suppress the virus lowers the side effects that accompany use of these drugs, and improves patient compliance with the drug-taking regimen and the patient's quality of life.

Prior to the studies which underlie the present invention, it was unknown whether ABC transporters could be disrupted by TM analogs. No means existed for predicting whether the rigidity of the structure of members of the superfamily would permit an inserted polypeptide to interfere with assembly of the TM domains into a fully functional structure. Further, no means exist to predict whether the strength of the interactions among TM domains were such that an inserted polypeptide would not be able to outcompete the endogenous TM domain. Finally, it could not be predicted how important for the function of the protein were the interactions among the various TM domains of ABC transporters.

These questions have now been answered for the ABC transporter superfamily. MDR1 is an important member of the superfamily because of its role in conferring resistance to chemotherapy to many human cancer cells. MDR1 performs this role by effluxing cancer drugs from the cell. During the studies resulting in the invention, TM analogs were made to a number of TM domains of MDR1. All of the analogs worked to inhibit the ability of cells expressing MDR1 to efflux substrates of the transporter. It is thus clear that the intramembrane portions of ABC transporters are not too rigid to permit inserted polypeptides to interfere with assembly or function of the ABC transporters, and that the interactions among endogenous domains are not so strong that they cannot be outcompeted by appropriately designed analogs. The structure and organization of MDR1 is similar to that of the other members of the superfamily. In view of the results with MDR1 TM analogs, it is clear that polypeptides based on transmembrane domains of a member of the ABC transporter superfamily interfere with the function of the targeted ABC transporter and can be used to inhibit the function of any targeted member of the superfamily.

Analogs to any of the TM domains of the targeted ABC transporter will provide at least some reduction in substrate transport. Analogs of TM domains indicated by structure-function analysis to be involved in substrate binding, however, are better at interfering with enzymatic function and are therefore stronger inhibitors of function than are analogs targeted to other TM domains. In preferred embodiments, therefore, the TM domain targeted by the analog is one predicted from structure-function analysis to be involved in substrate binding. In further preferred embodiments, the TM domain or domains targeted are those in which studies of mutations in the transporter have found residues which cannot be modified without some effect on transporter activity.

Analogs of these domains will generally have the greatest degree of effect in interfering with transporter function. As previously noted, however, analogs to any domain will cause at at least some inhibition of transporter activity and therefore are useful in interfering with ABC transporter function. In preferred embodiments, the TM analog inhibits at least 10%, 20%, 30%, 40%, 50%, 60%, 70%, 80%, 90%, or even more of the substrate transport of the target ABC transporter, with higher percentages of inhibition being preferred. The percentage by which a particular analog inhibits substrate transport can be readily determined by assays, such as those taught in the Examples.

An additional factor in selecting TM domains for which analogs will be made is the respective ease of synthesis. The practitioner will typically consider the amino acid sequence of the various TM domains of the transporter, especially those selected because they contain residues which have been found to be invariant or because of structure-function analysis, and select first those that are relatively easy to synthesize using whichever synthesis protocol he or she has selected.

Cells are generally understood in the art to be bounded by a plasma membrane (herein often referred to as the "cell membrane") comprising a lipid bilayer, in which proteins such as the ABC transporters are situated. See, generally, Alberts et al., Moelcular Biology of the Cell, Garland Publishing, Inc., New York (3$^{rd}$ Ed., 1994), Chapter 10. The cell membrane may be considered to have a surface facing on the cytosol, or the interior of the cell, and a surface facing to the exterior of the cell, or the extracellular space. Transmembrane proteins such as the ABC transporters are amphipathic, that is, they have regions that are hydrophobic and regions that are hydrophilic. Regions that pass through the membrane are hydrophobic and interact with the hydrophobic tails of the lipid molecules comprising the bilayer. Regions that are hydrophilic are exposed to water on either the cytosolic or the extracellular side of the membrane. Id.

In multipass transmembrane proteins, like the ABC transporters, the polypeptide chain crosses the membrane multiple times. Id. Portions of the protein about 20-30 amino acid residues in length with a high degree of hydrophobicity are long enough to cross the membrane as an α-helix and can be identified by a hydropathy plot. Id. Thus, the ABC transporters may be considered to be comprised of hydrophobic transmembrane domains connected by more hydrophilic intracellular (cytosolic) regions in the interior of the cell and one or more hydrophilic extracellular regions on the exterior of the cell.

Without wishing to be bound by theory, it is thought that ABC transporters assemble into a functional transporter and remain in position by virtue of non-covalent interactions among the various transmembrane domains of the transporter. It appears that the transmembrane domains of the ABC transporter are not so closely positioned by the cytosolic and extracellular regions connecting them to prevent analogs of the invention from infiltrating among the transmembrane domains. It further appears, however, that the analogs can sufficiently disrupt the interactions among the native transmembrane domains of the ABC transporter to disrupt the function of the transporter.

If the sequence of the ABC transporter is known, and the transmembrane domains are known, a polypeptide of the invention can be designed by simply following the amino acid sequence of the natural transmembrane domain, with one or more negatively charged residues added to the side of the polypeptide intended to be extracellular to assist in correct insertion of the polypeptide into the membrane. Thus, the polypeptides of the invention have a hydrophobic domain (which for convenience may be called the "A" region) mimicking the sequence of a transmembrane domain of the subject ABC transporter, and a negatively charged region (which for convenience may be called the "B" region), usually only a few amino acid residues in length, to assure that the A region is the portion of the polypeptide that inserts into the cell membrane and is thus oriented in the desired way within the membrane. It should be noted that the negatively charged residues do not need to be the terminal residues of the peptide to function, although they do need to be within 0-6 residues of the putative position of the membrane to assure correct orientation. Orientation of the molecule in the membrane increases the likelihood that the residues of the polypeptide will interact with the residues of intracellular portions of the subject ABC transporter in the same manner as the residues of the TM domain which the analog is intended to mimic (that is, the TM domain from which the analog is derived), thereby enhancing the ability of the analog to disrupt the function of the protein. Since the peptides are intended to insert into the membrane, leaving the charged B region exposed at the extracellular space, the polypeptides can be further described as having an extracellular end (comprising the B region) and a cytosolic end, denoting the portion of the polypeptide which will be closest to the cytosolic side of the membrane when the polypeptide is inserted in the membrane. Any residues between the negatively charged residues and the extracellular terminus of the peptide are generally selected to be non-hydrophobic and to contribute to the solubility of the molecule. Typically, the residues used in these positions are glycine and serine. Threonine can be used in these positions but is slightly more hydrophobic and is less preferred.

The hydrophobic nature of the transmembrane peptides makes the penetration of the polypeptide into the bilayer of the cell membrane highly probable. With regard to the B region, satisfactory results have been achieved using anywhere from 1 to 3 negatively charged residues, with 2 or 3 residues being preferred. Up to 5 residues may be used, but too large a charge may interfere with interactions with the extracellular regions of the TM domains of the ABC transporter. Therefore, if it is desired to use 5 or more negatively charged residues in the B region, the analog should be assayed in an in vitro assay to confirm whether the analog inhibits transport by the target ABC transporter. Positively charged residues in the B region tend to reduce or eliminate the ability of the polypeptide to disrupt the activity of the ABC transporter, and are not preferred.

Conveniently, the natural sequence of the transmembrane domain is used in designing the polypeptide. If desired, however, conservative substitutions of residues in the sequence can be made, or derivatized residues employed, so long as the substitutions or derivitizations do not reduce below a desired level the ability of the polypeptide to affect activity of the target ABC transporter. In preferred embodiments, the substitutions, derivatized, or synthetic amino residues can be used to enhance the ability of the polypeptide to affect the activity of the target ABC transporter. For example, if a phenylalanine in the natural TM domain is predicted to interact with a tryptophan in another domain of the ABC transporter, a cyanophenylalanine (which is known to interact more strongly with tryptophan than phenylalanine) may be substituted for phenylalanine in the analog to enhance the interaction with the tryptophan-containing domain of the target ABC transporter, thereby increasing the likelihood of disrupting the ABC transporter in cells in which the analog inserts itself into the cell membrane. An exemplary assay by which one of skill can determine the activity of an ABC transporter is set forth in the Examples.

In general, it is desirable for the hydrophobic portion of the analog (the "A region") to be a length to span approximately the whole lipid bilayer of the cell membrane. Once the analog infiltrates the can interact with many residues of the surrounding natural domains of the target ABC transporter.

If the natural sequence of the TM domains of the subject ABC transporter is not known, but the amino acid sequence of the transporter is known, any of a number of primary structure analysis programs can be used to predict the position and orientation of the transmembrane domains. Any of the following four programs, for example, are readily available on the internet: HMMTOP (found by entering "www." followed by "enzim.hu/hmmtop/"), TopPred 2 (found by entering "www." followed by sbc.su.se/~erikw/toppred2/; see, von Heijne, J. Mol. Biol., 225:487-494 (1992)), Tmpred (found by entering "www." followed by "ch.embnet.org/software/TMPRED_form.html"); see, Hofmann and Stoffel, Biol. Chem. Hoppe-Seyler 347:166 (1993)), and TMHMMM (found by entering "www." followed by "cbs.dtu.dk/services/TMHMM-1.0"). Table A sets forth the position and orientation of the domains of MDR1 predicted by these four programs.

In preferred embodiments, the TM portion of the analogs are long enough to span most of the cell membrane, since that increases the interactions among the analog and the TM domains of the ABC transporter and aids in stabilizing the analog in the ABC transporter. Shorter peptides can be used, but will usually have somewhat less stable associations with the transporters and may disrupt substrate transport less efficiently. This may not be important, however, if the cell is to be killed by a drug to which it has been rendered susceptible due to the impaired substrate transport of the transporter. Thus, analogs with only some 10 or so amino acid residues in the region expected to insert into the cell membrane can be used, as can peptides with lengths between 10-20 residues in this region of the peptide. In general, since about 20-30 amino acid residues are needed to span the plasma membrane, peptides with a hydrophobic region (following the sequence of a selected TM domain of the targeted ABC transporter) about this length are preferred. As previously noted, this hydrophobic region (the A region) will be augmented with one or more negatively charged residues (the B region, or "head group") to assist in correct orientation in insertion into the membrane.

TABLE A

Position and orientation of MDR1 transmembrane domains predicted by different programs

| | HMMTOP http://www.enzim.hu/hmmtop/ | TopPred 2 http://www.sbc.su.se/~erikw/toppred2/ | Tmpred http://www.ch.embnet.org/software/TMPRED_form.html | TMHMMM http://www.cbs.dtu.dk/services/TMHMM-1.0/ |
|---|---|---|---|---|
| TM1 | in 49-73 out | in 53-73 out | in 52-72 out | in 49-71 out |
| TM2 | out 117-141 in | out 121-141 in | out 116-140 in | out 114-136 in |
| TM3 | in 190-209 out | in 189-209 out | in 190-209 out | in 190-208 out |
| TM4 | out 214-238 in | out 213-233 in | out 214-231 in | out 214-232 in |
| TM5 | in 299-323 out | in 297-317 out | in 292-316 out | in 295-317 out |
| TM6 | out 328-352 in | out 327-347 in | out 328-346 in | |
| TM7 | in 712-736 out | in 708-728 out | in 708-733 out | out 710-732 in |
| TM8 | out 754-778 in | out 754-774 in | out 754-772 in | in 753-775 out |
| TM9 | in 833-852 out | in 854-874 out | in 846-874 out | out 852-874 in |
| TM10 | out 857-881 in | out 935-955 in | out 936-957 in | in 937-955 out |
| TM11 | in 937-956 out | in 973-993 out | in 974-992 out | out 974-996 in |
| TM12 | out 974-995 in | out 1063-1083 in | out 1065-1083 in | |

The position and orientation of the TM domains can also be determined empirically by art-recognized means, or by neural network algorithms (discussed infra).

An examination of Table A reveals some differences between the exact residues constituting the predicted TM domains. These differences can be readily accommodated. It will be noted that the goal is to create analogs that will insert into the cell membrane in an appropriate orientation to disrupt the function of a targeted ABC transporter. To achieve this goal, it is less important that the intracellular (cytosolic) end of the TM domain is defined. In the case of uncertainty, residues which may extend into the cytosol are omitted (to avoid hydrophilic residues that may impede insertion of the analog into the membrane, which as noted is hydrophobic) and a slightly longer portion of the extracellular region is used.

The end of the peptide that is predicted to be extracellular should bear a net negative charge. Any negatively charged residue, whether natural or synthetic, will suffice to orient the analog correctly. For ease of synthesis and to limit cost, aspartic acid and glutamic acid are the most commonly used. The residues added may be all aspartic acids, all glutamic acids, or a mixture of both. Aspartic acid is more preferred than glutamic acid since it is slightly more hydrophilic.

The length and hydrophobicity of the A region should be balanced against the desirability of maintaining sufficient solubility of the polypeptide to permit the analog to be easily administered. For this reason, it is desirable if the number of strongly hydrophobic residues (such as Phe, Trp, Tyr, and Ile) is limited to about 12-15 residues out of a 20-24 amino acid peptide. The solubility of the peptide will depend in part on the distribution of the hydrophobic residues in the peptide. If six or more hydrophobic residues occur together, in the middle of the analog or towards the cytosolic end of the molecule, the peptide will have a tendency to aggregate even during synthesis. Thus, TM domains having 6 or more hydrophobic residues together in the middle or the cytosolic end of the peptide are less preferred to be chosen as the basis for making analogs of the invention. Should such a domain be chosen, it is desirable to truncate the cytosolic end of the A region of the analog to reduce the number of hydrophobic residues occurring together and thereby increase the solubility of the molecule. The overall number of the residues at the extracellular end and in the portion to insert into the membrane should not exceed about 25 if the peptide is to be made by synthetic means since that tends to impair synthesis. It is preferable to avoid extending the peptide with sequence from the intracellular (cytosolic) portion of the sequence of the ABC transporter is likely to interfere with insertion into the membrane and hence the potency of the analogs, and is less preferred.

The solubility of any particular analog can be tested by contacting the analog with dimethyl sulfoxide ("DMSO"). Any analog which cannot be dissolved to form at least a 1 mM solution is not preferred. Analogs usually can be dissolved in DMSO to give a 5-10 mM stock solution. The stock solution is then diluted in culture medium (for in vitro use) or buffer (for in vivo use) to a concentration of 0.2%, thereby reducing the analogs to µM concentration. The solubility of the analog can be increased by including more of the amino acid sequence of the extracellular portion of the ABC transporter adjacent to the TM domain in question, or by adding a series of negatively charged amino acids, or by adding amino acids which are considered to contribute to solubility. Typically, glycine and serine are used for this purpose. Threonine can be used, but is modestly more hydrophobic and is less preferred. Alternatively, a combination of negatively charged amino acids and amino acid contributing to solubility are used to achieve the desired balance of negative charge and solubility The analogs of the invention have both in vitro and in vivo uses. In in vitro use, for example, they can be used to assist in purging a population of marrow cells harvested from a patient of any cancer cells which may be present before the cell population is infused into the patient. In this embodiment, cells of the cancer are examined to determine if the cancer is resistant to standard chemotherapeutic agents due to the action of an ABC transporter, and the ABC transporter is identified by standard techniques. The cells are then contacted with a TM analog appropriate for the particular ABC transporter rendering the cells resistant. For example, if the cancer cells are found to have the P-glycoprotein (MDR1), the cells are contacted with an MDR1 TM domain analog and either simultaneously or shortly thereafter (preferably within 48 hours, more preferably within 24 hours, even more preferably 1 to 4 hours) with a standard chemotherapeutic agent. Cells which had a functional P-glycoprotein will have the P-glycoprotein impaired in effluxing the chemotherapeutic agent from the cell and will therefore be killed by a lower concentration of the agent than would otherwise be necessary, decreasing the effect of the agent on the cells not expressing P-glycoprotein.

In in vivo uses, TM analogs of an ABC transporter protein, such as MDR1, MRP1, MRP2, or BCRP, respectively, are administered to a patient having a cancer expressing the particular protein. The analogs impair the functioning of the ABC transporter responsible for conferring resistance to chemotherapeutic agents to the cells of the cancer, rendering the cells more susceptible to killing by standard chemotherapeutic agents. In other in vivo uses, the TM analogs are administered to persons infected with HIV-1 who are taking a protease inhibitor. The ability of HIV-1 infected cells to efflux the protease inhibitor is impaired, resulting in a higher concentration of the protease inhibitor in the affected cell. This reduces the amount of the protease inhibitor which must be administered to the patient to achieve a virus-inhibiting dose in the infected cells, and the lower dose reduces the side effects of the protease inhibitor.

(b) Method for Measuring Anti-P-gp Activity

In addition to the TM analogs described above, the invention further provides a new method for measuring anti-P-glycoprotein ("P-gp") activity. As noted, P-gp activity in cancer cells provides those cells with resistance to many standard chemotherapeutic agents and is a major cause of the failure of standard cancer therapy. Accordingly, measuring the inhibition of P-gp activity is important in screening potential therapeutic agents. Currently, anti-P-gp activity is usually measured using fluoresence activated cell sorting (FACS), a method that requires considerable labor, an expensive, specialized FACS machine, and a specially trained technician. Further, the methods require the incubation of cells in suspension with fluorescent substrates. See, e.g., Feller et al., Br J Cancer, 72(3):543-549 (1995), Homola et al., Br J Cancer 73(7):849-855 (1996), Hafkemeyer et al., Biochem 37(46): 16400-9 (1998). Most cancer cells do not grow in suspension, which markedly reduces the utility of the current technique for measuring anti-P-gp activity in precisely the population of cells in which it is most important. Although the art has used FACS as a method for screening for P-gp inhibition for years, no less expensive and cumbersome method has been found.

Surprisingly, the present invention provides a simple and inexpensive method of measuring P-gp inhibition. The method does not require the use of suspended cells, and is conveniently performed in multiple well plates. Further, it is easily automated and suitable for high throughput screening.

The method provides a comparison of the efflux of a detectable substrate from cells having a P-gp in the absence of the inhibitor and in the presence of the inhibitor to determine if there is a difference. In preferred embodiments, the substrate is a fluorescent substrate which is taken up by cells, but effluxed from cells having a functional P-gp. In more preferred embodiments, the substrate is rhodamine 123, which is a substrate, for example, for MDR1 and MRP1, Lee et al., Biochemistry 37(11):3594-3601 (1998) or Fluo3, an analog of rhodamine has similar fluorescent properties to those of rhodamine and that is a substrate, for example, for MRP1 and MRP2 (Konig et al., Biochim Biophys Acta 1461(2):377-94 (1999)).

Cells having a P-gp are incubated with the substrate. The cells are then incubated in the presence of the putative inhibitor, while a control cohort of cells is incubated without the putative inhibitor. If the putative inhibitor is in fact an inhibitor of P-gp, the P-gp contacted with the inhibitor will be inhibited, and the cell will be less successful in effluxing the detectable substrate from the cell. If a fluorescent substrate is used, such cells will retain more fluorescence than cells not contacted with the putative inhibitor. If the putative inhibitor is not an inhibitor, there will be no significant difference in the amount of detectable substrate between the two cell populations.

It is worth noting that the methods of the invention can be employed whether or not the putative inhibitor is a TM analog or a more traditional chemical agent, so long as what is to be measured is the inhibition of the ABC transporter.

The method of the invention can be further enhanced by exposing cohorts of cells to successively higher concentrations of the putative inhibitor. Showing a dose-response curve is strong evidence that the putative inhibitor has an inhibitory effect. Further, reading of at least fluorescence substrates in the cells can be enhanced by contacting the cells with methanol or another alcohol. This fixes the cells and extracts the substrate, reducing the background and permitting easier reading. A detailed protocol for performing exemplary assays is set forth in Example 8.

Conveniently, the assay can be conducted in multi-well plates. The assay has been performed with success in 6-, 24-, and 96-well plates. The major adjustment between sizes is that, since the wells are larger in 6- and 24-well plates, the volumes of culture are larger and it is helpful to aspirate off the supernatant before reading the plate.

As noted, the method is adaptable for automation. In one embodiment, the invention relates to the formation of arrays of cells contacted with control media or with putative inhibitors, respectively. Such arrays can be scanned or read by array readers.

Typically, the array reader will have an optical scanner adapted to read the fluorescence of fluorescent substrate in cells in the array, operably linked to a device which reads and preferably prints out values corresponding to the fluorescence of cells exposed to the putative inhibitor relative to the controls. Optionally, the device is operably linked to a computer which can store on a drive in it, or accessible to it (for example, on an external drive or through the internet) one or more data files containing information on the values of the readings, the putative inhibitor tested, and, optionally, the concentrations of the putative inhibitor.

The methods of the invention can also be readily adapted to high throughput screening. High throughput ("HTP") screening is highly desirable because of the large number of compounds already developed in the larger pharmaceutical companies, because of the flood of new compounds now being synthesized by combinatorial chemistry, and because of the number of ABC transporters which are potential targets for to be inhibited. Using the invention, hundreds of chemical compositions can be tested on cells expressing an ABC transporter which is to be a target for inhibition, and the degree of resulting inhibition can be readily compared. Moreover, as many ABC transporters as may be desired can be tested at one time under the same conditions for their inhibition by the same inhibitor. For example, if a 96-well plate is used, a different ABC transporter can be tested in each row of wells. Those compositions with acceptable degrees of inhibition of a target ABC transporter can then be considered for further pre-clinical testing.

HTP screening can be facilitated by using automated and integrated culture systems, sample preparation, and analysis. These steps can be performed in regular labware using standard robotic arms, or in more recently developed microchip and microfluidic devices, such as those developed by Caliper Technologies Corp. (Palo Alto, Calif.), described in U.S. Pat. No. 5,800,690, by Orchid Biocomputer, Inc. (Princeton, N.J.), described in the Oct. 25, 1997 New Scientist, and by other companies, which provide methods of automated analysis using very low volumes of reagents. See, e.g., McCormick, R., et al., Anal. Chem. 69:2626-2630 (1997); Turgeon, M., Med. Lab. Management Rept, December 1997, page 1.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety An "ABC transporter" refers to a member of the superfamily of ATP-binding cassette transport proteins, a large family of proteins responsible for the translocation of a variety of compounds across membranes in prokaryotes and in eukaryotes. Examples of such transporters in humans include, but are not limited to, the 170 kDa P-gp, the 190 kDa multidrug resistance protein MRP (also known as "MRP1"), the 72 kDa breast cancer resistance protein known variously as "MXR," "BCRP" and "ABCP," multidrug resistance protein 2, or MRP2 (also known by the symbol "ABCC2"), cMOAT, ABCR, a gene encoding a rod photoreceptor specific protein, pABC11 (also known as "MOAT-C" and "MRP-5"), and ABC1 or "ATP cassette binding transporter 1. Murine members of this superfamily include the mouse Bcrp1/Mxr/Abcp gene, which is the mouse homolog of the human BCRP gene, the murine peroxisomal half-transporters ALDP, ALDRP, the 70 kDa PMP70, and PMP7-related protein P70R, and two murine glycoproteins that confer multidrug resistance, mdr1 (mdr1b) and mdr3 (mdr1a). Members of this superfamily in yeast include the weak-acid inducible ABC transporter Pdr12 and in fungi include CgCDR1, of the pathogen *Candida glabrata*. Prokaryotic member of this superfamily include the histidine permease of *Salmonella typhimurium* (composed of two integral membrane proteins, HisQ and HisM, and two copies of an ATP-binding subunit, HisP), the maltose-transport system of enterobacteria (composed of two integral membrane proteins, MalF and MalG, and two copies of an ATP-binding subunit, MalK), and the molybdate transport system of *Staphylococcus carnosus* encoded by "modABC." The term further encompasses subtypes of the named ABC transporters, and mutants and homologs thereof, along with the DNA sequences encoding the same. The multiple names of some members of the superfamily set forth above reflects the fact that several many members of the family were separently identified and studied by different laboratories, each of which assigned a name to the transporter.

The term "target ABC transporter" refers to a selected ABC transporter that is intended to be affected by the presence of a peptide of the invention. It is understood that the different ABC transporters noted above have transmembrane domains with different amino acid sequences. A transmembrane analog of the invention is designed to interfere with the substrate transport of a single ABC transporter by interactions with the transmembrane (TM) domains of that ABC transporter in a way which mimics (but may be stronger than) the interactions of those TM domains with the native TM domain the analog mimics.

The term "membrane" refers generally to a lipid bilayer. In most uses herein, the lipid bilayer under consideration is the plasma membrane that delimits a cell, but as required or suggested in context, may refer to other cellular membranes. The term membrane also encompasses where appropriate in context non-cellular bilayer structures, such as liposomes.

As used herein, the terms "ABC transporter polypeptide," "ABC transmembrane analog," "ABC TM analog" "TM analog" and "analog" refer to an isolated polypeptide or peptide having a first region (the "A region") at one end (or terminus) of the peptide and a second region, said second region (the "B region") being attached to said first region and continuing to a second end (or terminus) of the peptide. The second, "B" region further has an amino acid sequence which has at least 70% sequence identity to the sequence of a transmembrane domain of an ABC transporter, more preferably 75%, even more preferably 80%, and more preferably, a sequence identity which is any integer of percent identity between 81 and 100%, with higher percentages of sequence identity generally being preferred over lower percentages of sequence identity. The A region comprises 1 to 20 residues, more preferably 1 to 10 residues, and even more preferably 1 to 6 residues. The A region comprises negatively charged residues which confer a net negative charge on the A region; this net negative charge serves to orient the analog when it comes in contact with a cell membrane or other membrane. Optionally, the A region may contain residues, such as glycine and serine, which contribute to solubility. Threonine may also be used but is less preferred. The peptide can comprise natural or synthetic amino acids, such as cyanophenylalanine, or peptidomimetics, so long as the predominant linkage of the peptide is a peptide linkage. In preferred embodiments, the peptide is composed of natural and synthetic amino acids. In more preferred forms, the peptide consists of natural amino acids. Preferably, the ABC TM analog amino acid sequence is 8 to about 40 amino acids in length, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids in length, or any range therein. In more preferred embodiments, the peptide is 10-30 amino acids in length; in even more preferred forms the peptide is 15-30 amino acids in length. In even more preferred embodiments, the peptide is about 20 to about 25 amino acids in length, and in the most preferred embodiments, the peptide is 22 to 25 amino acids in length. Preferably, an ABC transporter polypeptide of the present invention substantially corresponds to a transmembrane domain of a ABC transporter. Preferred TM analogs, when contacted with a cell membrane or membrane structure (e.g., liposome) that contains a biologically active ABC transporter which the analog is intended to affect, inhibits the transport of one or more substrates of that ABC transporter in vitro, in vivo, or in situ.

The term "spontaneously inserts into a membrane" means that a peptide that is brought into contact with a membrane comprising a lipid bilayer will, under physiological conditions, arrange itself within the lipid bilayer such that the hydrophobic portion of the peptide is within the membrane, and any charged end is exposed to either surface of a membrane. In preferred embodiments, the membrane is the membrane bounding the cell, known as the cell membrane. As is known in the art, the cell membrane has a surface facing the cytosol, or interior, of the cell and a surface facing the exterior of the cell. The surface facing the exterior faces into the "extracellular" space. It is understood that while the molecules of the invention can insert into any membrane, in most embodiments they will be inserting into the cell membrane from the extracellular space and will therefore insert into the exterior surface of the cell. The analogs of the present invention have two ends. One end is intended to insert into the membrane. The distal end carries a net negative charge at physiological pH and is designed to protrude from the membrane into the extracellular space or to be exposed on the exterior surface of the cell. The charged end ensures that the analog inserts into the membrane in the desired direction.

The term "inhibit" in connection with a peptide of the invention refers to a decease in a biological activity of an ABC transporter protein of at least 10%, 20% 30%, 40%, 50%, 60%, 70% 80%, 90% or even higher, with higher percentages of inhibition being preferred over lower percentages.

The term "tumor cell" or "cancer cell" or "neoplastic cell" denotes a cell that demonstrates inappropriate, unregulated proliferation. A cell line is said to be "malignant" if, when the cell line is injected into a host animal, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal if cells from such tumors have human chromosomes.

The terms "treating cancer", "cancer therapy", and the like mean generally a treatment that causes any improvement in a mammal having a cancer wherein the improvement is due to treatment with a peptide of the invention. The improvement can be either subjective or objective. For example, if the mammal is human, the patient may note improved vigor or vitality or decreased pain as subjective symptoms of improvement or response to therapy. Alternatively, the clinician may notice a decrease in tumor size or tumor burden based on physical exam, laboratory parameters, tumor markers, or radiographic findings.

The phrase "inhibiting tumor [or cell] growth" generally means that the rate of increase in mass, size, number and/or the metabolism of cells and/or of tumors to which an agent is administered is slower as a result of the administration of the agent than that of cells and/or tumors not exposed to the agent. The growth of a cell line or tumor is said to be "inhibited" by an agent if, when assayed by means such as radioisotope incorporation into the cells, the cells contacted with the agent increase in number at a rate that is less than the proliferation rate of cells not so contacted ("control" cells), and preferably less than about 50% of the untreated cell proliferation rate. More preferably, the growth rate is inhibited by at least 80%. If growth is assayed by a means such as plating in methylcellulose, the growth of a cell line is said to be "inhibited" if the cells contacted with the agent give rise to less than the number of colonies that grow from a like number of cells which have not been contacted. Preferably, the number of colonies from cells contacted with the agent is less than about 70% of the number from control cells. More preferably, the number of colonies is decreased by at least 50%. "Inhibition of cell growth" also encompasses zero growth and, most importantly, consequent death of the tumor cells and eradication of the tumor. When measured in vivo, "inhibition of tumor growth" encompasses fewer or smaller tumors (for example, smaller diameter) as compared to control animals or patients to whom the agent is not administered. Progression of a tumor refers to events other than growth, such as morphological and physiological changes, and changes in gene and protein expression.

Inhibition can be evaluated by any accepted method of measuring whether growth or size of the tumor and/or increase in the number of cancerous or tumor cells has been slowed, stopped, or reversed. This includes direct observation and indirect evaluation such as subjective symptoms or objective signs. The clinician may notice a decrease in tumor size or tumor burden (number of tumors) based on physical exam, laboratory parameters, tumor markers, or radiographic findings. Alternatively, if the mammal is human, the patient may note improved vigor or vitality or decreased pain as subjective symptoms of improvement or response to therapy. Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonograms, computerized axial tomography scans, nuclear magnetic resonance scans and positron emission testing.

The term "residue" refers to an amino acid or amino acid mimetic incorporated in a oligopeptide by an amide bond or amide bond mimetic.

"Negatively charged" refers to those amino acids, amino acid derivatives, amino acid mimetics and chemical moieties that are negatively charged at physiological pH. Negatively charged amino acids include, for example, aspartic acid and glutamic acid. An "acidic" residue is a residue that is negatively charged at physiological pH.

"Positively charged" refers to those amino acids, amino acid derivatives, amino acid mimetics and chemical moieties that are positively charged at physiological pH. Positively charged amino acids include, for example, lysine and arginine. A "basic residue" is a residue that is positively charged at physiological pH.

"Neutral" refers to those amino acids, amino acid derivatives, amino acid mimetics and chemical moieties that are neither positively charged nor negatively charged at physiological pH.

"Consensus" sequence refers to peptides which are distinct from known ABC transporter sequences in critical structural features, but which are derived from consensus sequences of homologous ABC transporter transmembrane domains. Such consensus peptides may be derived by molecular modeling, optionally combined with hydrophobicity analysis and/or fitting to model helices, as non-limiting examples. Such modeling can be accomplished according to known method steps using known modeling algorithms, such as, but not limited to, ECEPP, INSIGHT, DISCOVER, CHEM-DRAW, AMBER, FRODO and CHEM-X. Such algorithms compare transmembrane domains between related ABC transporter, determine probable energy-minimized structures and define alternative consensus polypeptide fragments.

An amino acid or nucleic acid sequence of an ABC transporter of the present invention is said to "substantially correspond" to another amino acid or nucleic acid sequence, respectively, if the sequence of amino acids or nucleic acid in both molecules provides polypeptides having biological activity that is substantially similar, qualitatively or quantitatively, to the corresponding fragment of at least one ABC transporter transmembrane domain, or which may be synergistic when two or more transmembrane domains, consensus sequences or homologs thereof are present. Additionally or alternatively, such "substantially corresponding" sequences of ABC transporter polypeptides include conservative amino acid or nucleotide substitutions, or degenerate nucleotide codon substitutions wherein individual amino acid or nucleotide substitutions are well known in the art.

The term "modulates a biological property or activity" means that in the presence of a test transmembrane peptide a measurable biological parameter or event is increased or decreased relative to a control in the absence of said peptide. In preferred embodiments, the modulation is a decrease in transport by an ABC transporter. Examples of biological property or activity include: the conformation of the ABC transporter, association of the ABC transporter with other molecules, signal transduction, extracellular secretion of cellular proteins, conformational changes in proteins, changes in enzymatic activity, changes in metabolic activity, changes in affinity for a ligand, changes in levels of viral infection, changes in vasodilation, changes in heart rate, changes in bronchodilation, changes in endocrine secretions and changes in gut peristalsis. The ABC transporter biological activity need not be one that is limited to the precise in vivo role performed by the ABC transporter. The term also covers ABC transporter properties, such as viral protein binding, that are not part of the in vivo biological role of the ABC transporter. It further covers intrinsic properties of ABC transporters that are only disclosed by experimental manipulation in the laboratory, such as the ability of ABC transporters in artificial bilayers (e.g., liposomes) to interact with ABC transporter ligands.

"Efflux" is the process by which a cell pumps ions, cytotoxins, or other molecules and substrates from one compartment to another to alter their concentration in the compartments or to eliminate their presence in one compartment. Typically, this process results in the translocation of the substrate molecule from a cellular compartment to the surrounding extracellular medium, although it can also result in a translocation of the substrate molecule from one cellular compartment to another.

"ABC transporter ligands" refers to biological molecules that bind ABC transporters in vitro, in situ or in vivo, and may include hormones, neurotransmitters, viruses or receptor binding domains thereof, opsins, rhodopsins, nucleosides, nucleotides, coagulation cascade factors, odorants or pheromones, toxins, colony stimulating factors, platelet activating factors, neuroactive peptides, neurohumor, or any biologically active compounds, such as drugs or synthetic or naturally occurring compounds.

The term "effective amount" means a dosage sufficient to produce a desired result. The desired result can be subjective or objective changes in the biological activity of an ABC transporter, especially signal transduction. Effective amounts of the ABC transporter polypeptide or composition, which may also include a functional derivative thereof, are from about 0.01 micrograms to about 100 mg/kg body weight, and preferably from about 10 micrograms to about 50 mg/kg body weight, such 0.05, 0.07, 0.09, 0.1, 0.5, 0.7, 0.9, 1, 2, 5, 10, 20, 25, 30, 40, 45, or 50 mg/kg.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. Such substitutions preferably are made in accordance with the following list, which substitutions may be determined by routine experimentation provide modified structural and functional properties of a synthesized polypeptide molecule, while interacting with the ABC transporter, or inhibiting or mimicking biological activity, as determined by known ABC transporter activity assays.

| Original Residue | Exemplary Substitution |
|---|---|
| Ala | Gly; Ser |
| Arg | Lys |
| Asn | Gln; His |
| Asp | Glu |
| Cys | Se |
| Gln | Asn |
| Glu | Asp |
| Gay | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Put differently, the following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V); and

6) Phenylalanine (F), Tyrosine (Y), Tryptophan (W).

See also, Creighton, PROTEINS, W.H. Freeman and Company, San Francisco (1983). In addition, individual substitutions, deletions or additions which alter, add or delete a single amino acid or a small percentage of amino acids in an encoded sequence are also "conservatively modified variations".

The term "substantial identity" or "substantial similarity" in the context of a polypeptide indicates that a polypeptide comprises a sequence which has at least 70% sequence identity to a reference sequence, preferably 70%, more preferably 80%, even more preferably 85, 86, 87, 88, 89, or 90%, or most preferably 91, 92, 93, 93, 94, 95% or even higher sequence identity over a comparison window of about 10-20 amino acid residues, provided that the sequence is not identical to the reference sequence. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. Because the substituted amino acids have similar properties, the substitutions do not change the functional properties of the polypeptides. In some embodiments, the substituted amino acids are artificial amino acids, such as cyanophenylalanine, which have desirable properties. In these embodiments, the substitution of one, two, or three such artificial amino acids does not affect the calculation of sequence identity, with substitution of only two amino acids with synthetic amino acids being preferred, and with substitution of only one amino acid with a synthetic amino acid being more preferred.

An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution. An indication that two nucleic acid sequences are substantially identical is that the polypeptide which the first nucleic acid encodes is immunologically cross reactive with the polypeptide encoded by the second nucleic acid. Another indication that two nucleic acid sequences are substantially identical is that the two molecules hybridize to each other under stringent conditions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci.* USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35: 351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For purposes of this invention, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci.* USA 89:10915 (1989)) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, *Proc. Nat'l. Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al., 1992; Rossolini et al., Mol. Cell. Probes 8: 91-98 (1994)). The term nucleic acid is used interchangeably with gene, cDNA, and mRNA encoded by a gene.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, Tetrahedron Lett. 22:1859-1862 (1981), or by the triester method according to Matteucci, et al., J. Am. Chem. Soc., 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) ANTIBODIES, A LABORATORY MANUAL, Cold Spring Harbor Publications, New York, for a description of immunoassay formats and conditions that can be used to determine specific immunoreactivity.

ABC Transporter Transmembrane Polypeptides

ABC transporter transmembrane polypeptides of the present invention, or nucleic acids encoding therefor, include a finite set of substantially corresponding sequences as substitution peptides or polynucleotide which can be routinely obtained by one of ordinary skill in the art, without undue experimentation, based on the teachings and guidance presented herein. For a detailed description of protein chemistry and structure, see Schulz et al., PRINCIPLES OF PROTEIN STRUCTURE, Springer-Verlag, New York, 1978, and Creighton, T. E., PROTEINS: STRUCTURE AND MOLECULAR PROPERTIES, W.H. Freeman & CO., San Francisco, 1983, which are hereby incorporated by reference. For a presentation of nucleotide sequence substitutions, such as codon preferences, see F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel) at sections A.1.1-A.1.24, and Sambrook et al., MOLECULAR CLONING—A LABORATORY MANUAL (2nd Ed.), Vol. 1-3, Cold Spring Harbor Laboratory, Cold Spring Harbor, N.Y., 1989, at Appendices C and D. This manual is hereinafter referred to as "Sambrook, et al."

ABC transporter transmembrane polypeptides include homologous sequences and/or fragments of at least one of transmembrane domain of one or more ABC transporters or homologs thereof, which ABC transporter polypeptides do not occur naturally in an isolated form, or which are provided in an isolated and/or purified form not found in nature, or both. Homology to the native domain the analog is derived from assists in the interaction of the analog with the transmembrane portions of the ABC transporter protein. By modeling the TM portion of the ABC transporter to be inhibited, and the surrounding intramembrane portions of the transporter, it can be determined that some residues can be modified to strengthen the interaction and thereby to enhance the interference of the analog with the function of the transporter. Synthetic amino acids or amino acid mimetics can be used to improve the strength of the interaction. For example, if it is noted that the TM domain from which the analog is to be derived contains a phenylalanine which interacts with a tryptophan, the sequence of the analog can have a cyanophenylalanine substituted for the phenylalanine, since cyanophenylalanine interacts more strongly with tryptophan than does the natural amino acid.

In the context of the present invention, ABC transporter transmembrane polypeptides of greater than 15 amino acids are preferred such that the ABC transporter TM polypeptides are able to span the lipid bilayer. Shorter peptides may be used if desired, but tend to cause less robust disruption of ABC transporter function since there are fewer points at which the peptide can interact with the transmembrane domains of the ABC transporter. In preferred embodiments, the analogs are between 20 to 30 amino acids in length, with about 22-25 amino acids being more preferred.

There are two types of peptide bonds which can be used in the peptides of the invention, but preferably are not used because they add chemical instability: aspartic acid-serine and aspartic acid-glycine.

In one group of exemplary embodiments, peptides of the invention are derived from one or more of the 12 TM domains of MDR1. Non-limiting, illustrative examples of peptides derived from the 12 TM domains of MDR1 are set forth in the following list. The list identifies an analog for each domain. The transmembrane domain ("TM") to which the analog corresponds is identified by the letters "TM," followed by the number of the domain to which the analog pertains):

TM1 analog: VGTLAAIIHGAGLPLMMLVFGEDD (SEQ ID NO:1)

TM2 analog: DDYAYYYSGIGAGVLVAAYIQVS (SEQ ID NO:2)

TM3 analog: IGMFFQSMATFFTGFIVGFTGGD (SEQ ID NO:3)

TM4 analog: SSDDTLTLVILAISPVLGLSAAV (SEQ ID NO:4)

TM5 analog: LLIYASYALAFWYGTTLVLSGEGSSG (SEQ ID NO:5)

TM6 analog: DSGEYSIGQVLTVFFSVLIGAFSV (SEQ ID NO:6)

TM7 analog: AIINGGLQPAFAIIFSKIIGDD (SEQ ID NO:7)

TM8 analog: GDDSLFSLLFLALGIISFITF (SEQ ID NO:8)

TM9 analog: LAVITQNIANLGTGIIISFIYGDD (SEQ ID NO:9)

TM10 analog: GDDGWQLTLLLLAIVPIIA (SEQ ID NO:10)

TM11 analog: IFGITFSFTQAMMYFSYAGCFDD (SEQ ID NO:11)

TM12 analog: DDDLMSFEDVLLVFSAVVFGAMAVG (SEQ ID NO:12).

The TM5 analog set forth above is the strongest inhibitor of the MDR1 ABC transporter yet tested.

In a second group of exemplary embodiments, peptides of the invention are derived from one or more of the 6 TM domains of BCRP/MXR/ABCP. Non-limiting, illustrative examples of peptides of the invention derived from the 6 TM domains of BCRP/MXR/ABCP are set forth below. The analogs are identified as described in connection with MDR1, above:

TM1 analog: IIVTVVLGLVIGAIYFGLKNDSD (SEQ ID NO:13)

TM2 analog: DAGVLFFLTTNQCFSSVSAVELFVV (SEQ ID NO:14)

TM3 analog: LLPMRMLPSIIFTCIVYFMLGLKPDD (SEQ ID NO: 15)

TM4 analog: DDAFFVMMFTLMMVAYSASSMALAI (SEQ ID NO:16)

TM5 analog: LLMTICFVFMMIFSGLLVNLDD (SEQ ID NO:17)

TM6 analog: DDNHVALACMIVIFLTIAYLKLLF (SEQ ID NO:18).

In a third group of exemplary embodiments, peptides of the invention are derived from one or more of the TM domains of MRP1. Non-limiting, illustrative examples of peptides of the invention derived from the TM domains of MRP1 include the following:

TM1 analog: GIFLAPVFLVSPTLLGITTIDD (SEQ ID NO:19)

TM2 analog: DDSSGIMLTFWLVALVCALAIL (SEQ ID NO:20)

TM3 analog: FYVYFSLLLIQLVLSCFSDRSPLDD (SEQ ID NO:21)

TM4 analog: DDGYFYTVLLFVTACLQTLVL (SEQ ID NO:22)

TM5 analog: INMIWSAPLQVILALYLLWLDD (SEQ ID NO:23)

TM6 analog: DDGPSVLAGVAVMVLMVPVNAV (SEQ ID NO:24)

TM7 analog: TPFLVALCTFAVYVTIDENNILD (SEQ ID NO:25)

TM8 analog: DDFNILRFPLNILPMVISSIV (SEQ ID NO:26)

TM9 analog: AIGLFISFLSIFLFMCNHVSDD (SEQ ID NO:27)

TM10 analog: DDSQGIAVFGYSMAVSIGGILA (SEQ ID NO:28)

TM11 analog: VIGACIVILLATPIAAIIIPDD (SEQ ID NO:29)

TM12 analog: DDECVGNCIVLFAALFAVIS (SEQ ID NO:30).

In a fourth group of exemplary embodiments, peptides of the invention are derived from one or more of the 16 TM domains of MRP2. Non-limiting, illustrative examples of peptides of the invention derived from the 16 TM domains of MRP2 include the following:

TM1 analog: VLVWIPLGFLWLLAPWQLLHVDD (SEQ ID NO:31)

TM2 analog: DDQVFVGFLLILAAIELALVLT (SEQ ID NO:32)

TM3 analog: PAVRYTNPSLYLGTWLLVLLIDD (SEQ ID NO:33)

TM4 analog: DDFLSLFWILSILCGTFQFQTLI (SEQ ID NO:34)

TM5 analog: NLAYSCLFFISYGFQILILIFSAFSED (SEQ ID NO:35)

TM6 analog: DDKTFYMVLLKSFLLKLVNDIFTFV (SEQ ID NO:36)

TM7 analog: TYLWIGYLCAILLFTAALIQSFDD (SEQ ID NO:37)

TM8 analog: DDTNFMHMLWSSVLQIVLSIFFLW (SEQ ID NO:38)

TM9 analog: LGPSVLAGVGVMVLVIPINAILDD (SEQ ID NO:39)

TM10 analog: DDQLQCVVIFVFQLTPVLVSVVTFSV (SEQ ID NO:40)

TM11 analog: FTSITLFNILRFPLSMLPMMIDD (SEQ ID NO:41)

TM12 analog: DDQAIGLFSIFFIILAFVMNSVAFI (SEQ ID NO:42)

TM13 analog: LGLAQGIFVFIAHFWSAFGFVDD (SEQ ID NO:43)

TM14 analog: DDSTLVMICMATPVFTIIVIPLG (SEQ ID NO:44)

TM15 analog: AIRLELVGNLTVFFSALMMVIDD (SEQ ID NO:45)

TM16 analog: DDSSLTNCLFRILEAAGGQIII (SEQ ID NO:46).

The nucleotide and amino acids sequences of dozens of members of the ABC transporter superfamily are known in the art and accessible through GenBank and other publicly available databases. Citations to GenBank and other accession numbers and literature references for over thirty exemplary members of the superfamily are set forth in section 6, below. The transmembrane domains of these and other members of the superfamily can be readily determined by persons of ordinary skill in the art using art recognized procedures. One frequently used technique for determining putative TM domains is the TOP-PRED 2 software package, described in von Heijne, G., *J Mol Biol* 225:487-94 (1992). TOP PRED 2 and other programs are available on the internet, at the addresses set forth in the Introduction, above. Analysis by neural network systems provides another technique for determining TM domains. A leading study on this technique demonstrated that it had a 94% success rate in predicting the actual transmembrane domains in a rigorous cross-validation test on 69 proteins with experimentally determined locations of transmembrane domains. Rost, B. et al., *Protein Sci* 4:521-33 (1995).

Synthesis of Peptides

The peptides or fragments of ABC transporter transmembrane domains may be isolated from a natural source, chemically synthesized or produced recombinantly, in order to provide ABC transporter transmembrane polypeptides which mimic, modulate or inhibit binding of ligands to ABC transporters.

a. Chemical Synthesis of ABC Transporter Transmembrane Peptides

Transmembrane peptides of the present invention are made using well known peptide synthesis procedures, as described in e.g., Merrifield, Science 232: 341-347 (1986), Barany and Merrifield, THE PEPTIDES, Gross and Meienhofer, eds. (N.Y., Academic Press), pp. 1-284 (1979); and Stewart and Young, SOLID PHASE PEPTIDE SYNTHESIS (Rockford, Ill., Pierce), 2d Ed. (1984), all of which are incorporated by reference herein.

The peptides were synthesized by solid phase peptide synthesis on 431A Applied Biosystems Peptide Synthesizer utilizing Fmoc amino acid derivatives. To overcome aggregation that frequently occurs during the synthesis of hydrophobic peptides and leads to the blockage of the growing peptide chain, NovaSyn TGA resins (Nova Biochem, San Diego, Calif.) were used. The purity of the peptides was assessed by reverse phase HPLC and the structures confirmed by matrix-assisted laser-desorption time-of-flight (MALDI-TOF) mass spectrometry as described (Tarasova, N. I. et al., Adv. Exp. Med. Biol. 436:201-206 (1998)) and/or by HPLC coupled with an electrospray mass spectrometer. The purity of the peptides was assessed by reverse phase HPLC and the structures were confirmed by matrix-assisted laser-desorption mass spectrometry.

b. Recombinant Production of ABC Transporter Transmembrane Peptides

Nucleic acids that encode ABC transporter transmembrane peptides may be obtained by synthesizing, isolating or obtaining a nucleic acid sequence that encodes an ABC transporter protein, and subcloning a region of the sequence that encodes a desired transmembrane peptide.

i. Chemical synthesis of oligonucleotides

Oligonucleotides used in the present invention, including sequences that encode transmembrane peptides, are optionally chemically synthesized using the solid phase phosphoramidite triester method of Beaucage and Carruthers, *Tetrahedron Lett.*, 22(20): 1859-1862 (1981) using an automated synthesizer as described in Needham-VanDevanter et al., *Nucleic Acids Res.*, 12: 6159-6168 (1984). The chemically synthesized oligonucleotides are then purified by native acrylamide gel electrophoresis or by anion-exchange HPLC as described in Pearson and Regnier, *J. Chrom.*, 255: 137-149 (1983). The sequence of the synthetic oligonucleotide is verified, for example by using the chemical degradation method of Maxam and Gilbert in Grossman, L. and Moldave, D., eds. Academic Press, New York, *Methods in Enzymology*, 65:499-560 (1980).

The DNA sequences of the present invention coding for ABC TRANSPORTER transmembrane peptides protein can be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These modified DNA sequences may be prepared, for example, by mutating known sequences so that the mutation results in the deletion, substitution, insertion, inversion or addition of one or more amino acids in the encoded polypeptide using various methods known in the art. For example, the methods of site-directed mutagenesis described in Taylor et al., *Nucl. Acids Res.* 13, 8749-8764 (1985) and Kunkel, Proc. *Natl. Acad. Sci. USA* 82, 482-492 (1985) may be employed. In addition, kits for site-directed mutagenesis may be purchased from commercial vendors. For example, a kit for performing site-directed mutagenesis may be purchased from Amersham Corp. (Arlington Heights, Ill.). Both degenerate and non-degenerate mutations may be advantageous in producing or using the polypeptides of the present invention. For example, these mutations may permit higher levels of production, easier purification, or provide additional restriction endonuclease recognition sites. All such modified DNAs (and the encoded polypeptide molecules) are included within the scope of the present invention.

ii. Recombinant Isolation of ABC Transporter Transmembrane Peptide-Encoding Nucleic Acids Nucleic acids that encode ABC transporters can be isolated from genomic or cDNA libraries, subcloning the library into expression vectors, labeling probes, DNA hybridization, and the like, as described in Sambrook, supra.

Various methods of amplifying target sequences, such as the polymerase chain reaction (PCR), can also be used to prepare DNA encoding ABC TRANSPORTER transmembrane peptides or a peptide fragment thereof. In PCR techniques, oligonucleotide primers complementary to the two 3' borders of the DNA region to be amplified are synthesized. The polymerase chain reaction is then carried out using the two primers. See PCR PROTOCOLS: A GUIDE TO METHODS AND APPLICATIONS. (Innis, M, Gelfand, D., Sninsky, J. and White, T., eds.), Academic Press, San Diego (1990). Primers can be selected to amplify the entire regions encoding a full-length ABC transporter transmembrane peptides or to amplify smaller DNA segments as desired. Once selected sequences are PCR-amplified, oligonucleotide probes can be prepared from sequence obtained. These probes can then be used to isolate DNA's encoding ABC transporter transmembrane peptides or a peptide fragment thereof.

iii. Recombinant Expression of Transmembrane Peptide-Encoding Nucleic Acids

Once a nucleic acid encoding an ABC transporter transmembrane peptides or a peptide fragment thereof is isolated and cloned, the nucleic acid is expressed in a variety of recombinantly engineered cells to ascertain that the isolated nucleic acid indeed encodes the desired ABC TRANSPORTER transmembrane peptides or a peptide fragment thereof. The expression of natural or synthetic nucleic acids is typically achieved by operably linking a nucleic acid of interest to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith (1979), Gene, 8: 81-97; Roberts et al. (1987), *Nature*, 328:731-734; Berger and Kimmel, Guide to Molecular Cloning Techniques, *Methods in Enzymology* 152, Academic Press, Inc., San Diego, Calif. (Berger); Sambrook et al. (1989), MOLECULAR CLONING—A LABORATORY MANUAL (2nd ed.) Vol. 1-3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem. Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acids (e.g., coding sequences, promoters and vectors) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., (1981) *Tetrahedron Lett.*, 22:1859-1862; Matteucci, (1981) et al., *J. Am. Chem. Soc.*, 103:3185-3191; Caruthers, et al., (1982) *Genetic Engineering*, 4:1-17; Jones, chapter 2, Atkinson, et al., chapter 3, and Sproat, et al., chapter 4, in OLIGONUCLEOTIDE SYNTHESIS: A PRACTICAL APPROACH, Gait (ed.), IRL Press, Washington D.C. (1984); Froehler, et al., (1986) *Tetrahedron Lett.*, 27:469-472; Froehler, et al., (1986) *Nucleic Acids Res.*, 14:5399-5407; Sinha, et al. (1983) *Tetrahedron Lett.*, 24:S843-5846; and Sinha, et al., (1984) *Nucl. Acids Res.*, 12:4539-4557, which are incorporated herein by reference.

Derivatized Peptides and Peptidomimetics

The design of chemically modified peptides and peptide mimics which are resistant to degradation by proteolytic enzymes or have improved solubility or binding properties is well known.

Modified amino acids or chemical derivatives of ABC transporter peptides according to the present invention may contain additional chemical moieties or modified amino acids not normally a part of the protein. Covalent modifications of the peptide are thus included within the scope of the present invention. Such modifications may be introduced into an ABC transporter polypeptide by reacting targeted amino acid residues of the polypeptide with an organic derivatizing agent that is capable of reacting with selected side chains or terminal residues. The following examples of chemical derivatives are provided by way of illustration and not by way of limitation.

The design of peptide mimics which are resistant to degradation by proteolytic enzymes is well known, both for hormone agonist/antagonist and for enzyme inhibitor design. See e.g., Sawyer, in STRUCTURE-BASED DRUG DESIGN, P. Verapandia, Ed., NY 1997; U.S. Pat. No. 5,552,534; and U.S. Pat. No. 5,550,251, all of which are incorporated by reference.

Historically, the major focus of peptidomimetic design has evolved from receptor-targeted drug discovery research and has not been directly impacted by an experimentally-determined three-dimensional structure of the target protein. Nevertheless, a hierarchical approach of peptide→peptidomimetic molecular design and chemical modification has evolved over the past two decades, based on systematic transformation of a peptide ligand and iterative analysis of the structure-activity and structure-conformation relationships of "second generation" analogs. Such work has typically integrated biophysical techniques (x-ray crystallography and/or NMR spectroscopy) and computer-assisted molecular modeling with biological testing to advance peptidomimetic drug design.

The three-dimensional structural properties of peptides are defined in terms of torsion angles ($\Psi$, $\phi$, $\omega$, $\chi$) between the backbone amine nitrogen ($N^\alpha$), backbone carbonyl carbon ($C^1$), backbone methionine carbon ($C^\alpha$), and side chain hydrocarbon functionalization (e.g., $C^\beta$, $C^\lambda$, $C^\delta$, $C^\epsilon$; of Lys) derived from the amino acid sequence. A Ramachandran plot ($\Psi$ versus $\phi$) may define the preferred combinations of torsion angles for ordered secondary structures (conformations), such as $^\alpha$ helix, $^\beta$ turn, $^\gamma$ turn, or $^\beta$ sheet. Molecular flexibility is directly related to covalent and/or noncovalent bonding interactions within a particular peptide. Even modest chemical modifications by $N^\alpha$-methyl, $C^\alpha$-methyl or $C^\beta$-methyl can have significant consequences on the resultant conformation.

The $N^\alpha$—$C^\alpha$-C' scaffold may be transformed by introduction of olefin substitution (e.g., $C^\alpha$—$C^\beta$→C=C or dehydroamino acid or insertion (e.g., $C^\alpha$—C'→$C^\alpha$—C=C—C' or vinylogous amino acid. Also the $C^\beta$ carbon may be substituted to advance the design of so-called "chimeric" amino acids. Finally, with respect to N-substituted amides it is also noteworthy to mention the intriguing approach of replacing the traditional peptide scaffold by achiral N-substituted glycine building blocks. Overall, such $N^\alpha$—$C^\alpha$—C scaffold or $C^\alpha$—$C^\beta$ side chain modifications expand peptide-based molecular diversity (i.e., so-called "peptoid" libraries) as well as extend our 3-D structural knowledge of traditional $\Phi$-$\Psi$-$\chi$ space.

In one approach, such as disclosed by Sherman and Spatola, *J. Am. Chem. Soc.* 112: 433 (1990), one or more amide bonds are replaced in an essentially isosteric manner by a variety of chemical functional groups. For example, any amide linkage in any of the ABC transporter polypeptides can be replaced by a ketomethylene moiety, e.g. (—C(=O)—CH$_2$—) for (—(C=O)—NH—). A few of the known amide bond replacements include: aminomethylene or $\Psi$[CH$_2$NH]; ketomethylene or $\Psi$[COCH$_2$]; ethylene or $\Psi$[CH$_2$CH$_2$]; olefin or $\Psi$[CH=CH]; ether or $\Psi$[CH$_2$O]; thioether or $\Psi$[CH$_2$S]; tetrazole or $\Psi$[CN$_4$]; thiazole or $\Psi$[thz]; retroamide or $\Psi$[NHCO]; thioamide or $\Psi$[CSNH]; and ester or $\Psi$[CO$_2$]. These amide bond surrogates alter conformational and H-bonding properties that may be requisite for biological activity at ABC transporter targets. Furthermore, such backbone replacements can impart metabolic stability towards peptidase cleavage relative to the parent peptide. The discovery of yet other nonhydrolyzable amide bond isostere has particularly impacted the design of protease inhibitors, and these include: hydroxymethylene or Ψ[CH(OH)]; hydroxyethylene or Ψ[CH(OH)CH$_2$] and Ψ[CH$_2$CH(OH)]; dihydroxyethylene or (Ψ[CH(OH)CH(OH)], hydroxyethylamine or Ψ[CH(OH)CH$_2$N], dihydroxyethylene and C$_2$-symmetric hydroxymethylene. Such backbone modifications have been extremely effective, as they may represent transition state mimics or bioisosteres of the hypothetical tetrahedral intermediate (e.g., Ψ[C(OH)$_2$NH]) for this class of proteolytic enzymes. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Both peptide backbone and side chain modifications may provide prototypic leads for the design of secondary structure mimicry, as typically suggested by the fact that substitution of D-amino acids, N$^\alpha$—Me-amino acids, C$_\alpha$—Me amino acids, and/or dehydroamino acids within a peptide lead may induce or stabilize regiospecific $^\beta$-turn, $^\gamma$-turn, $^\beta$-sheet, or $^\alpha$-helix conformations. To date, a variety of secondary structure mimetics have been designed and incorporated in peptides or peptidomimetics. The $^\beta$-turn has been of particular interest to the area of receptor-targeted peptidomimetic drug discovery. This secondary structural motif exists within a tetrapeptide sequence in which the first and fourth C$^\alpha$ atoms are $\leq 7$ Å separated, and they are further characterized as to occur in a nonhelical region of the peptide sequence and to possess a ten-membered intramolecular H-bond between the i and i→4 amino acid residues. One of the initial approaches of significance to the design of $^\beta$-turn mimetics was the monocyclic dipeptide-based template which employs side chain to backbone constraint at the i+1 and i+2 sites. Over the past decade a variety of other monocyclic or bicyclic templates have been developed as $^\beta$-turn mimetics. Monocyclic $^\beta$-turn mimetic has been described that illustrate the potential opportunity to design scaffolds that may incorporate each of the side chains (i, i+1, i+2 and i+3 positions), as well as five of the eight NH or C=O functionalities, within the parent tetrapeptide sequence, tetrapeptide sequence modeled in type I-IV $^\beta$-turn conformations. Similarly, a benzodiazepine template has shown utility as a $^\beta$-turn mimetic scaffold which also may be multisubstituted to simulate side chain functionalization, particularly at the i and i+3 positions of the corresponding tetrapeptide sequence modeled in type I-VI $^\beta$-turn conformations. A recently reported γ-turn mimetic, illustrates an innovative approach to incorporate a retroamide surrogate between the i and i→1 amino acid residues with an ethylene bridge between the N$^1$ (i.e., nitrogen replacing the carbonyl C') and N atoms of the i and i+2 positions, and this template allows the possibility for all three side chains of the parent tripeptide sequence. Finally, the design of a $^\beta$-sheet mimetic provides an attractive template to constrain the backbone of a peptide to that simulating an extended conformation. The $^\beta$-sheet is of particular interest to the area of protease-targeted peptidomimetic drug discovery.

Aromatic amino acids may be replaced with D- or L-napthylalanine, D- or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1-C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO$_3$H) threonine, serine, tyrosine.

Other substitutions may include unnatural hyroxylated amino acids made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amino acid of said peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of ABC transporter polypeptides of the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

Tyrosyl residues may be modified by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to certain chemical moieties. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of ABC transporter polypeptides of the present invention may include hydroxylation of proline and lysine, phosphorylation of hydroxyl groups of seryl or threonyl residues, methylation of the alpha-amino groups of lysine, arginine, and histidine side chains (T. E. Creighton, PROTEINS: STRUCTURE AND MOLECULAR PROPERTIES, W.H. Freeman & Co., San Francisco, pp. 79-86 (1983)), acetylation of the N-terminal amine, methylation of main chain amide residues (or substitution with N-methyl amino acids) and, in some instances, amidation of the C-terminal carboxyl groups, according to known method steps.

Such derivatized moleties may improve the solubility, absorption, permeability across the blood brain barrier biological half life, and the like. Such moleties or modifications of ABC transporter polypeptides may alternatively eliminate or attenuate any possible undesirable side effect of the protein and the like. Moleties capable of mediating such effects are disclosed, for example, in *Remington's Pharmaceutical Sciences,* 16th ed., Mack Publishing Co., Easton, Pa. (1980).

Such chemical derivatives of ABC transporter polypeptides also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased binding affinity or modulation for ABC transporters, which is desired for therapeutic compositions comprising ABC transporter polypeptides, antibodies thereto or fragments thereof. Such peptide derivatives are well-known in the art, as well as method steps for making such derivatives using carbodiimides active esters of N-hydroxy succinimmide, or mixed anhydrides, as non-limiting examples.

Variation upon the sequences of ABC transporter polypeptides of the present invention may also include: the addition of one or more (e.g., two, three, four, or five) lysine, arginine or other basic residues or one, or more (e.g., two, three, four, or five) glutamate or aspartate or other acidic residues at one end of the peptide, where "acidic" and "basic" are as defined herein. Negative charges can also be introduced by the addition of carboxyl, phosphate, borate, sulfonate or sulfate groups. Such modifications may increase the alpha-helical content of the peptide by the "helix dipole effect". They also can provide enhanced aqueous solubility of the peptide, and allow the correct insertion of peptides into a membrane structure.

In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of gamma-lactam or other types of bridges. See, e.g., Veber and Hirschmann, et al., *Proc. Natl. Acad. Sci. USA,* 1978 75 2636 and Thorsett, et al., *Biochem Biophys. Res. Comm.,* 1983 111 166. The primary purpose of such manipulations has not been to avoid metabolism or to enhance oral bioavailability but rather to constrain a bioactive conformation to enhance potency or to induce greater specificity.

The above examples of peptide scaffold- or nonpeptide template-based peptidomimetic agonists or antagonists illustrate various strategies to elaborate bioactive conformation and/or pharmacophore models. Thus, although the 3D structures of many ABC transporters remains elusive, the development of pharmacophore models using the hierarchial approach in peptide→peptidomimetic structure-based drug design is promising.

Purification of ABC Transporter Transmembrane Peptides

The polypeptides of this invention may be purified to substantial purity by standard techniques, including selective precipitation with such substances as ammonium sulfate, column chromatography, immunopurification methods, and others. See, for instance, R. Scopes, *Protein Purification: Principles and Practice,* Springer-Verlag: New York (1982), incorporated by reference. For example, the ABC transporter transmembrane peptides proteins and polypeptides produced by recombinant DNA technology are purified by a combination of cell lysis (e.g., sonication) and affinity chromatography or immunoprecipitation with a specific antibody to ABC transporter transmembrane peptides or a peptide fragment thereof. For fusion products, subsequent digestion of the fusion protein with an appropriate proteolytic enzyme releases the desired polypeptide. The proteins may then be further purified by standard protein chemistry techniques. A purified protein preferably exhibits a single band on an electrophoretic gel. Those of skill are reminded that the methods should take into account the hydrophobic nature of the peptides.

Detection of ABC Transporter Transmembrane Peptide Gene Products

ABC transporter transmembrane peptides or a peptide fragment thereof to may be detected or quantified by a variety of methods. Preferred methods involve the use of specific antibodies.

a. Detection of ABC transporter transmembrane peptides by immunoassay i. Antibody Production Methods of producing polyclonal and monoclonal antibodies are known to those of skill in the art. See, e.g., Coligan (1991), CURRENT PROTOCOLS IN IMMUNOLOGY, Wiley/Greene, N.Y.; and Harlow and Lane (1989), ANTIBODIES: A LABORATORY MANUAL, Cold Spring Harbor Press, NY; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), Nature, 256:495-497. Such techniques include antibody preparation by selection of antibodies from libraries of recombinant antibodies in phage or similar vectors. See, Huse et al. (1989), Science, 246:1275-1281; and Ward et al. (1989) Nature, 341:544-546. For example, in order to produce antisera for use in an immunoassay, a polypeptide is isolated as described herein. For example, recombinant protein is produced in a transformed cell line. An inbred strain of mice or rabbits is immunized with the peptide using a standard adjuvant, such as Freund's adjuvant, and a standard immunization protocol. Alternatively, a synthetic peptide derived from the sequences disclosed herein and conjugated to a carrier protein can be used an immunogen.

A number of immunogens may be used to produce antibodies specifically reactive with ABC transporter transmembrane peptides or a peptide fragment thereof. Recombinant protein is the preferred immunogen for the production of monoclonal or polyclonal antibodies. Naturally occurring protein may also be used either in pure or impure form. Synthetic peptides made using the ABC transporter transmembrane peptides or a peptide fragment thereof sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein such as ABC transporter transmembrane peptides or a peptide fragment thereof is mixed with an adjuvant and injected into an animal of choice (e.g., a mouse, rat, rabbit, pig, goat, cow, horse, chic ken, etc.) at intervals of 1-4 weeks. The immunogen may be conjugated to a carrier protein can be used an immunogen. The animal's immune response to the immunogen preparation is monitored by taking test bleeds and determining the titer of reactivity to the ABC transporter transmembrane peptides or a peptide fragment thereof. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-ABC transporter transmembrane peptides or even ABC transporter transmembrane peptides from other cell types or species or a peptide fragment thereof, using a competitive binding immunoassay (see, e.g., Harlow and Lane, supra, at pages 570-573). Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, Eur. J. Immunol. 6:511-519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) Science 246:1275-1281.

ii. Immunoassays

A particular protein can be measured by a variety of immunoassay methods. For a review of immunological and immunoassay procedures in general, see BASIC AND CLINICAL IMMUNOLOGY, 7th Edition (D. Stites and A. Terr, eds.) 1991. Moreover, the immunoassays of the present invention can be performed in any of several configurations, which are reviewed extensively in ENZYME IMMUNOASSAY, E. T. Maggio, ed., CRC Press, Boca Raton, Fla. (1980); "Practice and Theory of Enzyme Immunoassays," P. Tijssen, in LABORATORY TECHNIQUES IN BIOCHEMISTRY AND MOLECULAR BIOLOGY, Elsevier Science Publishers B. V. Amsterdam (1985); and, Harlow and Lane, ANTIBODIES, A LABORATORY MANUAL, supra, each of which is incorporated herein by reference.

Immunoassays to ABC transporter transmembrane peptides, peptidomimetics or subfragments thereof may use a polyclonal antiserum raised against a peptide or peptidomimetic of the invention. This antiserum is selected to have low cross-reactivity against other (other non-ABC transporter transmembrane peptides or other ABC transporter transmembrane peptides) peptides and any such cross-reactivity is removed by immunoabsorption prior to use in the immunoassay.

Immunoassays in the competitive binding format can be used for the crossreactivity determinations. For example, a reference peptide antigen of the invention can be immobilized to a solid support. The ability of other molecules (other ABC transporter transmembrane peptides, or non-ABC transporter transmembrane peptides, or unknowns) to compete with the binding of antisera which recognize the immobilized reference peptide antigen is measured. The ability of such molecules to compete with the binding of an antiserum or antibody to the immobilized reference peptide is compared to a standard molecule, such as the reference peptide antigen itself. The percent crossreactivity is calculated, using standard calculations. Antisera with less than 10% crossreactivity to crossreacting molecules are selected and pooled. Any cross-reacting antibodies are optionally removed from the pooled antisera by immunoabsorption with cross-reacting molecules.

The immunoabsorbed and pooled antisera are then used in a competitive binding immunoassay to compare the binding of a second protein to that of the reference peptide antigen. In order to make this comparison, the two molecules are each assayed at a wide range of concentrations and the amount of each molecule required to inhibit 50% of the binding of the antisera to the immobilized reference peptide antigen is determined. If the amount of the second protein required is less than 10 times the amount of the reference peptide used to make the antibody, then the second protein is said to specifically bind to an antibody generated to the reference peptide antigen.

The presence of a desired polypeptide (including peptide, translation product, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

Detection of ABC Transporter Transmembrane Peptide Sequences, Peptides and Peptidomimetics that Optimally Inhibit ABC Transporter Biological Properties And Functions Peptides or peptide variants of the invention that modulate biological activity of ABC transporters are generally identified as follows. Peptide sequences are selected from the transmembrane domains of the ABC transporter to be targeted. The transmembrane domains are readily ascertained by the application of computer models to known sequences. Computer modeling and comparison with known transmembrane peptide sequences are also used to define the orientation of the peptide sequence in the membrane, thus allowing the determination of the end of the peptide sequence that is towards the extracellular aspect of the plasma membrane. The selection of a preferred transmembrane domain to be targeted is largely empirical. We have found that peptides derived from transmembrane domains which are predicted from structure-function relationship to be involved with substrate binding, such as domains 6, 11, and 12, of MDR1, are particularly effective inhibitors of function.

Upon selection of a peptide sequence, a reference transmembrane sequence is synthesized and systematically modified to identify variants (or analogs) that have improved properties. The modifications introduce a negative charge at the extracellular end of the peptide sequence. Negative charges may be added in the form of acidic amino acid residues such as Asp or Glu. The number of acidic residues that is added is typically from 1 to 3 depending upon the hydrophobicity of the peptide sequence and the subsequent necessity to increase the solubility of the peptide. Further, preferable peptides have a neutral charge at the end of the peptide that is oriented towards the intracellular aspect of the plasma membrane. Thus, the overall hydrophobic nature of such a transmembrane peptide will result in insertion into a membrane and the negative charge at the extracellular end will result in the peptide having the same orientation as the ABC transporter transmembrane domain from which it is derived. Insertion into the membrane may be tested by fluorescent microscopy of labeled peptide analogs using methodology known to those of skill in the art.

The ability of the peptide or peptide variants to modulate activity of the targeted ABC transporter can be determined by a variety of assays known in the art. Typically, the modulatory ability of the peptide is determined by testing the ability of the peptide to increase or to inhibit transport of the molecule or ion which is normally transported by the targeted ABC transporter. For example, many ABC transporters function as ATP-dependent cytotoxin efflux pumps. Thus, if a particular ABC transporter is known to be reduce the cytoplasmic concentration of a particular drug, the efflux of the drug can be determined in first in the absence and then in the presence of the ABC transporter transmembrane polypeptide. For example, a cell line expressing the human BCRP gene can be used to test whether an ABC transporter transmembrane polypeptide inhibits transport by the breast cancer resistance protein by measuring the efflux of a drug such as mitoxantrone or doxorubicin and then testing the efflux of the same drug in like cells contacted with the ABC transporter transmembrane polypeptide.

Peptides may be tested for other properties, including the following:
  enhanced ability to modulate ABC transporter activity;
  increased resistance to proteolysis;
  improved solubility;
  longer or shorter half-life, particularly in culture medium or a biological fluid such as plasma or whole blood;
  improved ability to insert into a membrane compartment, especially in a particular orientation, by means known in the art.

Variant peptides may also be synthesized having any one or more of the following modifications:
  conservative or non-conservative substitution of any of the amino acid residues;
  deletion or addition of residues at any position;
  chemical modification at any residue;
  peptidomimetic analogs of the reference peptide.

Variant peptides can be rationally designed and/or screened for using high throughput screening methodologies applied to combinatorial libraries. Methods of generating combinatorial libraries and screening such libraries using high-throughput methods are well known to those of skill in the art (see, e.g., Baum, *C&EN* (Feb. 7, 1994), pp. 20-26 and references cited therein).

These variant peptides are also tested for the any of the above-listed properties. In general, a variant peptide is considered to have improved properties relative to the reference peptide if a given measurable property or parameter associated with the peptide has a value that is at least 10%, preferably at least 30%, more preferably at least 75%, and most preferably at least 95% better than the value for the reference peptide.

The relative ability of the modified peptides (as compared to the reference peptide) to modulate an ABC transporter biological activity is tested as follows. A cell line that expresses an ABC transporter and exhibits a ABC transporter-mediated biological activity is exposed to either the reference or the modified peptide under identical conditions, and the biological property of the ABC transporter is measured in the absence or presence of either peptide. Examples of cell lines, ABC transporter expressed by the cell line, and ABC transporter-regulated properties measured include the following:

any cell that stably expresses MDR1, including cells that are genetically engineered to express MDR1, including HeLa cells;

any cell that stably expresses BCRP/MXR, especially attached cells, including cells that are genetically engineered to express BCRP/MXR;

any cell that stably expresses MOAT-B (MRP4), MOAT-C (MOAT5), MOAT-D (MRP3), or MOAT-E, including cells that are genetically engineered to express MOAT-B (MRP4), MOAT-C (MOAT5), MOAT-D (MRP3), or MOAT-E, such as CHO cells.

The inhibitory activity is measured by exposing ABC transporter-expressing cells to a range of concentrations of a test antagonist, and measuring a biological property or activity associated with that ABC transporter. The test concentrations can range from 1 nanomolar to 100 micromolar, depending on peptide solubility and affinity. Initial screening is performed using 10-fold dilutions, such as 50, 5, 0.5, 0.05 micromolar. Then, the lowest active concentration is lowered in decrements of 10% to determine the lowest effective concentration. The property measured can be efflux of a cytotoxin (for example, efflux of doxorubicin by a cell expressing MDR1), or production of a measurable metabolic response (e.g., altered ion flux or translocation, altered phosphorylation, altered protein synthesis or degradation, altered cellular morphology, altered secretion, altered production of particular components such as soluble inositol phosphates, binding of a virus and subsequent infection, tumor growth, chemotaxis, mitogenic response, cell growth activation, and secretion.)

The following is a list of human ABC transporters which have a role in efflux of drugs from cells, rendering them resistant to the drugs, or which have other physiological roles. The list further provides references to the scientific literature setting forth information of the amino acid sequence or nucleotide sequence information on the transporter, or both, and the GenBank accession numbers or other publicly available nucleotide and amino acid sequence information:

Multidrug resistance protein (MDR)1 (P-glycoprotein 1) (Natl Center for Biotechnology (NCBI) Entrez browser (www.ncbi.nlm.nih.gov/) protein accession number P08183 (hereafter, references to protein accession numbers available through the NCBI Entrez browser are referred as "NCBI Entrez protein," followed by the accession number; references to nucleotide sequences encoding a protein available through the NCBI Entrez browser are referred to simply as NCBI Entrez nucleotide," followed by the accession number);

MDR 3 (P-glycoprotein 3) (NCBI Entrez protein P21439);

BCRP/MXR/ABCP (Doyle et al., Proc Natl Acad Sci USA 95:15665-70 (1998), (NCBI Entrez nucleotide AF093771). BCRP is a highly efficient transporter responsible for enhanced efflux of the topoisomerase I inhibitor topotecan as well as the topoisomerase II inhibitor mitoxantrone (Maliepaard et al., Cancer Res 59:4559-63 (1999));

Mitoxantrone resistance protein (MXR) 2 (NCBI Entrez nucleotide AF093772);

MRP (Deeley and Cole, Semin Cancer Biol 8:193-204 (1997));

MRP2/cMOAT/ABCC2 (Hagmann et al., Eur J Biochem 265:281-9 (1999); Kuwano et al., Anticancer Drug Des 14:123-31 (1999)). Absence of this transporter from the hepatocyte canalicular membrane is the molecular basis of Dubin-Johnson syndrome, characterized by conjugated hyperbilirubinemia and by impaired secretion of anionic conjugates from hepatocytes into bile. (Tsujii et al., Gastroenterology 117(3):653-60 (1999)). ABC transporter transmembrane polypeptides of the invention are useful reagents to study the mechanism by which impairment of this protein in vitro impacts hepatocyte function.

MOAT-B (MRP4) (Belinsky and Kruh, Br J Cancer 80:1342-9 (1999));

MOAT-D (MRP3) (Belinsky and Kruh, supra).

ABC1, the gene product of which is involved in cholesterol efflux. Defects in ABC 1 are the cause of Tangier disease, frequently characterized by premature coronary artery disease. (Rust et al., Nat Genet. 22(4):316-8 (1999)). ABC transporter transmembrane polypeptides of the invention targeted to this transporter are useful reagents to study the mechanism by which impairment of this transporter affects cholesterol efflux and results in the disease.

pABC11 (also known as MOAT-C and MRP5), shown to confer resistance to $CdCl_2$ and potassium antimonyl tartrate (Yamanouchi et al., J Biol Chem 274:23541-8 (1999).

MOAT-E (ARA), a 1503 residue transporter expressed in kidney and liver which functions as an organic anion transporter involved in cellular detoxification (Belinsky and Kruh, Br J Cancer 80:1342-9 (1999));

ABCR, a rod photoreceptor specific ABC transporter. Mutations in this gene are associated with at least four inherited retinal dystrophies. (Shroyer et al., Vision Res 39(15):2537-44 (1999)). Polypeptides inhibiting this transporter in rod cells in vitro are useful reagents for detecting other retinal dystrophies associated with this transporter.

ABCB3, GenBank accession number NM_000544. Polypeptides inhibiting this transporter in vitro are useful reagents for detecting disfunctions associated with defects in this transporter;

ABCG1, GenBank accession number NM_004915. Polypeptides inhibiting this transporter in vitro are useful reagents for detecting disfunctions associated with defects in this transporter;

ABCG2, GenBank accession number NM_004827. Polypeptides inhibiting this transporter in vitro are useful reagents for detecting disfunctions associated with defects in this transporter;

ABCB7, GenBank accession number NM_004299. Polypeptides inhibiting this transporter in vitro are useful reagents for detecting disfunctions associated with defects in this transporter;

ABCA3, GenBank accession number NM_001089. Polypeptides inhibiting this transporter in vitro are useful reagents for detecting disfunctions associated with defects in this transporter; and Human peroxisomal ABC-transporter, GenBank accession number NM_005050. Polypeptides inhibiting this transporter in vitro are useful reagents for detecting disfunctions associated with defects in this transporter.

The following is a list of mouse ABC transporters which have a role in efflux of drugs from cells, rendering them resistant to the drugs, or which have otherwise shown important physiological roles:

Bcrp1/Mxr/Abcp encodes a 657-amino acid protein which shares 81% amino acid identity with the human BCRP. (Allen et al., Cancer Res 59:4237-41 (1999)). Cells expressing Bcrp1 show high resistance to topotecan, mitoxantrone and doxorubicin. Id. Expressing Bcrp1 in mice therefore provides an excellent animal model for testing ABC transporter transmembrane polypeptides of the invention for their ability to inhibit the activity of Bcrp1 and, by extension, BCRP.

mdr1(mdr1b) (Grul et al., Biochem Pharmacol 58:1191-9 (1999)). This protein is a homolog of human MDR1 and useful for evaluating ABC transporter transmembrane polypeptides of the invention for their ability to inhibit mdr1 activity in an animal model;

mdr3 (mdr1a) (Grul et al., supra). This protein is a homolog of human MDR3 and useful for evaluating ABC transporter transmembrane polypeptides of the invention for their ability to inhibit mdr1 activity in an animal model;

ALDP, ALDRP, PMP70, and P70R, are four mammalian peroxisome half-transporters expressed in mice. The pattern of expression differs by tissue type. (Berger et al., Eur J Biochem 265:719-27 (1999)). Polypeptides inhibiting these transporters in cells in vitro are useful reagents for determining the role these transporters play in each cell type; and TAPL (TAP-like ABC transporter), GenBank accession no. AB027520. Polypeptides inhibiting this transporter in cells in vitro are useful reagents for determining the role this transporter plays in cells.

In addition to these ABC transporters in humans and animals, ABC transporters play important roles in microscopic eukaryotes and in prokaryotes, including important pathogens of humans and animals and commercially important organisms such as yeast. These transporters have a role in efflux of drugs from cells, rendering the cells resistant to the drugs, or have otherwise shown important physiological roles:

CgCDR1 is an ABC transporter responsible for resistance to azole antifungal agents in the human fungal pathogen *Candida glabrata*, which infects AIDS patients. (Sanglard et al., Antimicrob Agents Chemother 43:2753-65 (1999)). The gene is similar to the *C. albicans* CDR gene. Id. GenBank accession no. AF109763;

Pdr12 is a weak-acid inducible ABC transporter in yeast. Cells grown in the presence of sorbic acid and loaded with the dye fluorescein immediately efflux the dye upon the addition of an energy source in the form of glucose. (Holyoak et al., J Bacteriol 181:4644-52 (1999)).

The binding-protein-dependent maltose-transport system of enterobacteria is composed of two integral membrane proteins, MalF and MalG, and two copies of an ATP-binding subunit, MalK. (Schmees et al., Eur J. Biochem 266:420-430 (1999)).

*Salmonella typhimurium* histidine permease is composed of two integral membrane proteins, HisQ and HisM, and two copies of an ATP-binding subunit, HisP, which hydrolyze ATP, thereby providing energy for translocation. (Nikaido and Ames, J Biol Chem 274:26727-35 (1999));

*Salmonella typhimurium* oxd-6, GenBank accession no. U94729;

*Yersinia enterocolitica* ABC transporter enterochelin/enterobactin gene cluster, GenBank accession no. AF082879;

*Mycoplasma agalactiae* p48 gene, GenBank accession no. AJ132423;

abcZ ABC transporter gene, *Nesseria meningitidis*, GenBank accession no. AF165318.

The following is a list of exemplary transmembrane peptides that have ABC transporter-antagonist properties. Each exemplary peptide is an analog of the transmembrane domain of the transporter designated by the number following the term "TM" in the phrase "TM analog":

For the P-glycoprotein ABC transporter encoded by the MDR1 gene:
TM1 analog: VGTLAAIIHGAGLPLMMLVFGEDD (SEQ ID NO:1)
TM2 analog: DDYAYYYSGIGAGVLVAAYIQVS (SEQ ID NO:2)
TM3 analog: IGMFFQSMATFFTGFIVGFTGGD (SEQ ID NO:3)
TM4 analog: SSDDTLTLVILAISPVLGLSAAV (SEQ ID NO:4)
TM5 analog: LLIYASYALAFWYGTTLVLSGEGSSG (SEQ ID NO:5)
TM6 analog: DSGEYSIGQVLTVFFSVLIGAFSV (SEQ ID NO:6)
TM7 analog: AIINGGLQPAFAIIFSKIIGDD (SEQ ID NO:7)
TM8 analog: GDDSLFSLLFLALGIISFITF (SEQ ID NO:8)
TM9 analog: LAVITQNIANLGTGIIISFIYGDD (SEQ ID NO:9)
TM10 analog: GDDGWQLTLLLLAIVPIIA (SEQ ID NO:10)
TM11 analog: IFGITFSFTQAMMYFSYAGCFDD (SEQ ID NO:11)
TM12 analog: DDDLMSFEDVLLVFSAVVFGAMAVG (SEQ ID NO:12).

For the Breast Cancer Resistance Protein, encoded by gene known variously as BCRP/MXR1/ABCP:
TM1 analog: IIVTVVLGLVIGAIYFGLKNDSD (SEQ ID NO:13)
TM2 analog: DAGVLFFLTTNQCFSSVSAVELFVV (SEQ ID NO:14)
TM3 analog: LLPMRMLPSIIFTCIVYFMLGLKPDD (SEQ ID NO:15)
TM4 analog: DDAFFVMMFTLMMVAYSASSMALAI (SEQ ID NO:16)
TM5 analog: LLMTICFVFMMIFSGLLVNLDD (SEQ ID NO:17)
TM6 analog: DDNHVALACMIVIFLTIAYLKLLF (SEQ ID NO:18).

Nucleic Acids Encoding Peptides of the Invention

In one aspect this invention provides isolated nucleic acid molecules comprising nucleotide sequences encoding the peptides of the invention. The nucleic acids are useful for expressing the peptides in host cells. Persons of skill will appreciate that nucleic acids encoding any particular peptide of the invention can be determined by reference to standard lists of the codons that encode each of the amino acids comprising any one of the peptides. For example, the exemplary TM5 peptide, LLIYASYALAFWYGTTLVLSGEGSSG (SEQ ID NO:5), which is particularly preferred as an an inhibitor of MDR1 activity, is encoded by the following DNA sequence: CTT CTT ATC TAC GCG AGC TAT GCG CTC GCC TTC TGG TAT GGT ACT ACT CTT GTG CTT TCT GGT GAG GGT TCT TCT GGT (SEQ ID NO:47. Persons of skill will further recognize that, due to the degeneracy of the genetic code, a large number of alternative nucleic acid sequences could be designed to encode this or any other of the peptides set forth herein, including the exemplary peptides set forth in the preceding section.

A nucleic acid comprising sequences of the invention can be amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB).

A wide variety of cloning and in vitro amplification methodologies are well-known to persons skilled in the art. PCR methods are described in, for example, U.S. Pat. No. 4,683,195; Mullis et al (1987) Cold Spring Harbor Symp. Quant. Biol. 51:263; and Erlich, ed., PCR TECHNOLOGY, (Stockton Press, NY, 1989). Engineered versions of the nucleic acids can be made by site-specific mutagenesis of other polynucleotides encoding TM domains, or by random mutagenesis caused by increasing the error rate of PCR of the original polynucleotide with 0.1 mM $MnCl_2$ and unbalanced nucleotide concentrations.

A. Expression Vectors

The invention provides expression vectors for expressing nucleic acids encoding the structural analogs of the invention. Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., MOLECULAR CLONING—A LABORATORY MANUAL, Cold Spring Harbor Laboratory, Cold Spring Harbor, N.Y., (1989) and CURRENT PROTOCOLS IN MOLECULAR BIOLOGY, F. M. Ausubel et al., eds., (Current Protocols, Greene Publishing Associates, Inc. and John Wiley & Sons, Inc.) ("Ausubel"). Useful promoters for such purposes include a metallothionein promoter, a constitutive adenovirus major late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter.

Expression vectors useful in this invention depend on their intended use. Such expression vectors must, of course, contain expression and replication signals compatible with the host cell. Expression vectors useful for expressing proteins and peptides of the invention include viral vectors such as retroviruses, adenoviruses and adeno-associated viruses, plasmid vectors, cosmids, and the like. Viral and plasmid vectors are preferred for transfecting mammalian cells. The expression vector pcDNA3 (Invitrogen, San Diego, Calif.), in which the expression control sequence comprises the CMV promoter, provides good rates of transfection and expression.

A variety of means are available for delivering polynucleotides to cells including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. See also U.S. Pat. No. 5,272,065 (Inouye et al.); METHODS IN ENZYMOLOGY, vol. 185, Academic Press, Inc., San Diego, Calif. (D. V. Goeddel, ed.) (1990) or M. Krieger, GENE TRANSFER AND EXPRESSION—A LABORATORY MANUAL, Stockton Press, New York, N.Y., (1990). Recombinant DNA expression plasmids can also be used to prepare the polynucleotides of the invention for delivery by means other than by gene therapy, although it may be more economical to make short oligonucleotides by in vitro chemical synthesis.

B. Recombinant cells

The invention also provides recombinant cells comprising an expression vector for expression of the nucleotide sequences of this invention ("host cells"). Host cells can be selected for high levels of expression in order to purify the protein. The cells can be prokaryotic cells, such as E. coli, or eukaryotic cells. Useful eukaryotic cells include yeast and mammalian cells. The cell can be, e.g., a recombinant cell in culture or a cell in vivo.

Therapeutic Embodiments

The compositions containing the present ABC transporter transmembrane peptides, or a cocktail thereof (i.e., with other molecules, including other peptides of the invention), can be administered for therapeutic purposes. Typically, the molecules of the present invention are brought into contact with cells, thereby permitting the peptides to insert into the membrane of the cells, which inhibits the activity of the targeted ABC transporter.

In one group of embodiments, the ABC transporter transmembrane peptides of the invention are administered to sensitize cancer cells to standard chemotherapeutics, which chemotherapeutics are then administered to kill the cancer cells. For example, a cancer cell having a functional MDR1 ABC transporter is contacted with one of the exemplary MDR1 transmembrane peptides set forth in the preceding section. Assembly of MDR1 transporters is disrupted, thereby reducing the activity of the transporter, and rendering the cell more susceptible to being killed by standard chemotherapeutic agents. Standard chemotherapeutic agents which can be used to kill a cell include topotecan, mitoxantrone, doxorubicin, daunorubicin, etoposide, vincristine, and vinblastine. Such susceptiblity can be readily measured in in vitro assays, as set forth in the Examples, or in standard animal models by comparing the rate of growth of tumors in animals to which are administered first an ABC transporter analog and then a chemotherapeutic agent to the growth of the same type of tumor in animals to which are administered just the ABC transporter transmembrane peptides or just the chemotherapeutic agent. The chemotherapeutic agents noted above in connection with MDR1-expressing cells can also be used in connection with cells expressing MRP1 or BCRP. For cells expressing MRP2, the chemotherapeutic agents which can be used include topotecan, mitoxantrone, doxorubicin, cisplatin, CPT-11, SN-38, and camptothesins.

a. Pharmaceutical Compositions

The compositions for administration may be in the form of a solution, suspension, tablets, pill, capsule, powder, gel, cream, lotion, ointment, aerosol or the like. In a preferred embodiment, the compositions for administration comprise a solution of the ABC transporter transmembrane peptides dissolved in a pharmaceutically acceptable carrier, preferably an aqueous carrier. A variety of aqueous carriers can be used, e.g., buffeted saline and the like. These solutions are sterile and generally free of undesirable matter. These compositions may be sterilized by conventional, well known sterilization techniques. In certain embodiments, the ABC transporter transmembrane peptides are provided in powder form.

The ABC transporter transmembrane peptides and analogs may be combined with conventional excipient, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the ABC transporter in these formulations can vary widely, and will be selected primarily based on fluid volumes, viscosities, body weight and the like in accordance with the particular mode of administration selected and the patient's needs.

b. Administration and Dosage

The pharmaceutical composition or medium that comprises an ABC transporter transmembrane peptide is administered orally, parenterally, enterically, gastrically, topically, subcutaneously, rectally, locally or systemically. For example, the compounds can be injected into the bloodstream using a cannula or catheter; the vein or artery is selected to maximize delivery of cells to the affected tissue(s). Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980). It is recognized that the ABC transporter transmembrane polypeptides and related compounds described above, when administered orally, should be protected from digestion. This is typically accomplished either by complexing the protein with a composition to render it resistant to acidic and enzymatic hydrolysis or by packaging the polypeptide in an appropriately resistant carrier such as a liposome. Means of protecting proteins from digestion are well known in the art.

In therapeutic applications, compositions are administered to a patient suffering from a disease or condition that in an amount sufficient to fully or partially arrest symptoms of the disease or conditions and its complications. An amount adequate to accomplish this is defined as a "therapeutically effective dose." Amounts effective for this use will depend upon the severity of the condition to be treated and the general state of the patient's health.

Generally, the dosage to be administered is the amount necessary to modulate an ABC transporter biological activity. It is understood that the dosage of a ABC transporter polypeptide of the present invention will be dependent upon the age, sex, health, and weight of the recipient, kind of concurrent treatment, if any, frequency of treatment, and the nature of the effect desired. The ranges of effective doses provided herein are not intended to limit the inventors and represent preferred dose ranges. The most preferred dosage will be tailored to the individual subject, as is understood and determinable by one of skill in the art, without undue experimentation. It is contemplated that the compounds will be administered under the guidance of a physician, who will determine the exact dosages, monitor the progress of the treatment, and determine whether a given administration is successful and sufficient, or whether subsequent administrations are needed.

The concentration of compounds to be administered at a given time and to a given patient will vary from 0.1 µg-100 mg and preferably 0.1-10 mg per day per patient. The dosage and mode of administration may be chosen to achieve and optionally maintain a local concentration in fluids that contact the target cells of about 0.001-50 µg/ml, preferably 0.1-10 µg/ml. Dosages from 0.1 up to about 100 mg per patient per day may be used, particularly when the drug is administered to a secluded site and not into the blood stream, such as into a body cavity or into a lumen of an organ. Substantially higher dosages are possible in topical administration.

Single or multiple administrations of the compositions may be necessary depending on the dosage and frequency as required and tolerated by the patient. In any event, the composition should provide a sufficient quantity of the peptides of this invention to effectively treat the patient.

C. Gene Therapy

The present invention provides packageable ABC transporter transmembrane peptide-encoding nucleic acids for the transformation of cells in vitro and in vivo. These packageable nucleic acids can be inserted into any of a number of well known vectors for the transfection and transformation of target cells and organisms.

The nucleic acids are transfected into cells, ex vivo or in vivo, through the interaction of the vector and the target cell. The ABC transporter transmembrane peptide-encoding nucleic acid, under the control of a promoter, then expresses the ABC transporter transmembrane peptide, thereby modulating the biological activity of a target ABC transporter.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992) 256:808-813; Nabel and Felgner (1993) *TIBTECH* 11: 211-217; Mitani and Caskey (1993) *TIBTECH* 11: 162-166; Mulligan (1993) *Science* 926-932; Dillon (1993) *TIBTECH* 11: 167-175; Miller (1992) *Nature* 357: 455-460; Van Brunt (1988) *Biotechnology* 6(10): 1149-1154; Vigne (1995) *Restorative Neurology and Neuroscience* 8: 35-36; Kremer and Perricaudet (1995) *British Medical Bulletin* 51(1) 31-44; Haddada et al. (1995) in CURRENT TOPICS IN MICROBIOLOGY AND IMMUNOLOGY Doerfler and Böhm (eds) Springer-Verlag, Heidelberg Germany; and Yu et al., GENE THERAPY (1994) 1:13-26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682-691; Rose U.S. Pat. No. 5,279,833; Brigham (1991) WO 91/06309; and Felgner et al. (1987) *Proc. Natl. Acad. Sci. USA* 84: 7413-7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) J. NIH Res. 4:43, and Cornetta et al. *Hum. Gene Ther.* 2:215 (1991)). Widely used retroviral vectors include those based upon murine leukemia virus (MuLV), gibbon ape leukemia virus (GaLV), simian immunodeficiency virus (SIV), human immunodeficiency virus (HIV), and combinations thereof. See, e.g., Buchscher et al. (1992) *J. Virol.* 66(5) 2731-2739; Johann et al. (1992) *J. Virol.* 66 (5):1635-1640 (1992); Sommerfelt et al., (1990) *Virol.* 176:58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology, Third Edition* Paul (ed) Raven Press, Ltd., New York and the references therein, and Y et al., GENE THERAPY (1994), supra).

AAV-based vectors are also used to transduce cells with target nucleic acids, e.g., in the in vitro production of nucleic acids and peptides, and in in vivo and ex vivo gene therapy procedures. See, West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invest.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251-3260;

Tratschin, et al. (1984) *Mol. Cell. Biol.*, 4:2072-2081; Hermonat and Muzyczka (1984) *Proc. Natl. Acad. Sci. USA*, 81:6466-6470; McLaughlin et al. (1988) and Samulski et al. (1989) *J. Virol.*, 63:03822-3828. Cell lines that can be transformed by rAAV include those described in Lebkowski et al. (1988) *Mol. Cell. Biol.*, 8:3988-3996.

i. In Vitro Gene Transfer

It is expected that those of skill in the art are knowledgeable in the numerous expression systems available for expression of DNA encoding ABC transporter transmembrane peptides or a peptide fragment thereof. No attempt to describe in detail the various methods known for the expression of proteins in prokaryotes or eukaryotes is made here.

There are several well-known methods of introducing nucleic acids into bacterial and animal cells, any of which may be used in the present invention. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation, micro-injection of the DNA directly into the cells, infection with viral vectors, etc.

For in vitro applications, the delivery of nucleic acids can be to any cell grown in culture, whether of bacterial, plant or animal origin, vertebrate or invertebrate, and of any tissue or type. Contact between the cells and the genetically engineered nucleic acid constructs, when carried out in vitro, takes place in a biologically compatible medium. The concentration of nucleic acid varies widely depending on the particular application, but is generally between about 1 μmol and about 10 mmol. Treatment of the cells with the nucleic acid is generally carried out at physiological temperatures (about 37° C.) for periods of time of from about 1 to 48 hours, preferably of from about 2 to 4 hours.

In one group of embodiments, a nucleic acid is added to 60-80% confluent plated cells having a cell density of from about $10^3$ to about $10^5$ cells/mL, more preferably about $2\times10^4$ cells/mL. The concentration of the suspension added to the cells is preferably of from about 0.01 to 0.2 μg/mL, more preferably about 0.1 μg/mL.

ii. In Vivo Gene Transfer

Alternatively, the ABC transporter transmembrane peptide encoding nucleic acids can also be introduced into target cells in vivo, using recombinant methods which are known to those of skill in the art. The insertion of genes into cells for the purpose of medicinal therapy is a rapidly growing field in medicine which has enormous clinical potential. Research in gene therapy has been on-going for several years, and has entered human clinical trials. Zhu, et al., *Science*, 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature*, 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.*, 298:278-281 (1989), incorporated herein by reference, describes the in vivo transfection of lungs of mice with a functioning prokaryotic gene encoding the intracellular enzyme chloramphenicol acetyltransferase (CAT).

Formulations suitable for administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials. Injection solutions and suspensions can be prepared from sterile powders, granules, and tablets of the kind previously described.

For in vivo administration, pharmaceutical compositions that comprise ABC transporter transmembrane peptide-encoding nucleic acids are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., *Methods in Enzymology*, Academic Press, New York. 101:512-527 (1983); Mannino, et al., *Biotechniques*, 6:682-690 (1988); Nicolau, et al., *Crit. Rev. Ther. Drug Carrier Syt.*, 6:239-271 (1989), and Behr, *Acc. Chem. Res.*, 26:274-278 (1993). Still other methods of administering therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In preferred embodiments, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the preparations may be administered through endoscopic devices.

The nucleic acid can also be administered in an aerosol inhaled into the lungs (see, Brigham, et al., *Am. J. Sci.*, 298 (4):278-281 (1989)) or by direct injection at the site of disease (Culver, *Human Gene Therapy*, MaryAnn Liebert, Inc., Publishers, New York. pp. 70-71 (1994)).

Effective doses of the compositions of the present invention will vary depending upon many different factors, including means of administration, target site, physiological state of the patient, and other medicants administered. Thus, treatment dosages will need to be titrated to optimize safety and efficacy. In determining the effective amount of the vector to be administered, the physician evaluates the particular nucleic acid used, the disease state being diagnosed; the age, weight, and condition of the patient, circulating plasma levels, vector toxicities, progression of the disease, and the production of anti-vector antibodies. The size of the dose also will be determined by the existence, nature, and extent of any adverse side-effects that accompany the administration of a particular vector. Doses ranging from about 10 ng to 1 g, 100 ng to 100 mg, 1 μg to 10 mg, or 30-300 μg DNA per patient are typical. Doses generally range between about 0.01 and about 50 mg per kilogram of body weight; preferably between about 0.1 and about 5 mg/kg of body weight or about $10^8$-$10^{10}$ or $10^{12}$ particles per injection. In general, the dose equivalent of a naked nucleic acid from a vector is from about 1 µg to 100 µg for a typical 70 kilogram patient, and doses of vectors which include a retroviral particle are calculated to yield an equivalent amount of inhibitor nucleic acid.

Prior to infusion, blood samples are obtained and saved for analysis. Between $10^8$ and $1\times10^{12}$ vectors are infused intravenously over 60-200 minutes. Vital signs and oxygen saturation by pulse oximetry are closely monitored. Blood samples are obtained 5 minutes and 1 hour following infusion and saved for subsequent analysis. At the physician's discretion, reinfusion is repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Vector infusion is slowed or discontinued depending upon the severity of the reaction.

In vivo gene transfer may be practiced in a variety of hosts. Preferred hosts include mammalian species, such as humans, non-human primates, dogs, cats, cattle, horses, sheep, and the like.

EXAMPLES

The following examples are simply embodiments of the invention and are not intended to limit the invention. A person of ordinary skill in the art can modify and/or adapt the invention for various applications without undue experimentation, without departing from the generic concept of the present invention. Therefore, such adaptations and modifications are within the scope and range of the present invention.

Example 1

This example illustrates synthesis of ABC transporter TM polypeptides derived from ABC transporter TM domains.

The peptides were synthesized by solid phase peptide synthesis on 432A or 433A Applied Biosystems Peptide Synthesizers equipped with conductivity monitoring units utilizing Fmoc amino acid derivatives. The synthesis was performed with conditional blocking of unreacted amino groups with acetic anhydride for easier purification of the resulting peptides. To overcome aggregation that frequently occurs during the synthesis of hydrophobic peptides and leads to the blockage of the growing peptide chain, NovaSyn TGA resins (Nova Biochem, San Diego, Calif.) were used. The purity of the peptides was assessed by reverse phase HPLC and the structures confirmed by matrix-assisted laser-desorption time-of-flight (MALDI-TOF) mass spectrometry as described (Tarasova, N. I. et al., Adv. Exp. Med. Biol. 436:201-206 (1998)) and/or by HPLC coupled with an electrospray mass spectrometer.

Example 2

This Example shows the design of appropriate ABC transporter TM polypeptides for an exemplary ABC transporter.

Antagonists to P-gp and other transmembrane proteins were designed utilizing the available models of P-gp topology. Considerable evidence reveals that the $NH_2$-terminal half of P-gp contains 6 TM segments. (Loo, T. W. et al., *J. Biol. Chem.* 270:843-848 (1995)); Kast, C., et al., *Biochemistry* 34:4402-4411 (1995); Kast, C. et al., *J. Biol. Chem.* 271:9240-9248 (1996)). However several models were proposed for the COOH-terminal half of P-gp. (Loo, T. W. et al., Biochemistry, 38, 5124-5 129 (1999). We synthesized the antagonists based on recent models, starting from the one that is based on hydropathy analysis (FIG. 1). Transmembrane portions (underlined sequences in FIG. 1) were synthesized with addition of aspartates to the extracellular ends.

Example 3

This Example discusses the testing of ABC transporter TM polypeptides for activity.

The activity of the antagonists was tested in KB 8-5 cells which express human P-gp (described in Hrycyna et al.; Biochemistry 37:13660-73 (1998)). Analyses of P-gp transport activity were conducted by fluorogenic substrate accumulation assays utilizing fluorescence activated cell sorting (FACS) analysis, as described in Dey, S. et al., Biochemistry 38:6630-9 (1999). Calcein-AM, bodipy-veramil, rodamine 123 and bodipy-taxol (purchased from Molecular Probes (Eugene, Oreg.) were used as P-gp substrates. Cyclosporin A is known to completely inhibit drug transport activity of P-gp at 5 µM (Dey, S. et al., Biochemistry, 38:6630-9 (1999)) and served as a positive control. The cells were incubated with the substrates in the presence or absence of the ABC transporter TM polypeptides. In these assays, cells with functional P-gp accumulate less substrate and are therefore less fluorescent, whereas inhibition of P-gp results in increased accumulation of fluorescent compounds, and cells which therefore have higher fluorescence. In initial screens, 5-10 µM stock solutions of TM peptides in DMSO were diluted in medium to give 10-50 µM solutions. Active compounds were then tested at progressively lower concentrations.

Example 4

This Example sets forth exemplary ABC transporter TM polypeptides, some of which are used in the succeeding examples. Peptides corresponding to the proposed TM domains 1, 2, 6, 11 and 12 of P-gp (FIG. 1) were synthesized as described in Example 1. Each peptide was modified at the putative extracellular terminal end with negatively charged residues, such as aspartic acid or glutamic acid, to assure the correct orientation of the peptide in the plasma membrane. The substitution by negatively charged moieties on the extracellular terminus of the TM peptides is important for correct orientation of the peptide. The synthetic peptides were as follows, with the negatively charged extracellular residues in bold:

TM1: H-Val-Gly-Thr-Leu-Ala-Ala-Ile-Ile-His-Gly-Ala-Gly-Leu-Pro-Leu-Met-Met-Leu-Val-Phe-Gly-Glu-Asp-Asp-OH (SEQ ID NO:1)

TM2: H-Asp-Asp-Tyr-Ala-Tyr-Tyr-Tyr-Ser-Gly-Ile-Gly-Ala-Gly-Val-Leu-Val-Ala-Ala-Tyr-Ile-Gln-Val-Ser-OH (SEQ ID NO:2)

TM6: H-Asp-Ser-Gly-Glu-Tyr-Ser-Ile-Gly-Gln-Val-Leu-Thr-Val-Phe-Phe-Ser-Val-Leu-Ile-Gly-Ala-Phe-Ser-Val-OH (SEQ ID NO:6)

TM11: H-Ile-Phe-Gly-Ile-Thr-Phe-Ser-Thr-Gln-Ala-Met-Met-Tyr-Phe-Ser-Tyr-Ala-Gly-Cys-Phe-Asp-Asp-OH (SEQ ID NO:11)

TM12: H-Asp-Glu-Asp-Val-Leu-Leu-Val-Phe-Ser-Ala-Val-Val-Phe-Gly-Ala-Met-Ala-Val-Gly-Gln-Val-Ser-Ser-PheOH (SEQ ID NO:50).

The following list sets forth, in single letter code, the TM domain sequences for MDR1 and exemplary analogs to each domain. In this list, the term "TM" for each pair or triplet of sequences refers first to the putative transmembrane domain of MDR1, with the residue numbers of the domain in the amino acid sequence of MDR1 indicated, followed by the amino acid residues of the TM domain, and then by the amino acid sequence of an exemplary analog. The sequences are aligned to facilitate comparison. In reviewing the peptides, it will be recalled that while the residues are listed left to right, the analogs are designed to insert into the membrane so that the residues are in the same position as in the TM domain of the ABC transporter. Since the ABC transporter protein is continuous, one TM domain (usually considered to be an alpha helix) will connect to an extracellular portion which then connects to a second TM domain, which traverses the cell membrane in an orientation opposite to the first. Thus, the end of the analog which carries the negatively charged "B region" depends on the orientation of the TM domain from which the analog is derived.

TM1 (residues 49-73)
LYMVVGTLAAIIHGAGLPLMMLVFG (SEQ ID NO:51)
Analog:
VGTLAAIIHGAGLPLMMLVFGEDD (SEQ ID NO:1)
TM2 (117-139)
YYSGIGAGVLVAAYIQVSFWCLAA (SEQ ID NO:52)
Analog:
DDYAYYYSGIGAGVLVAAYIQVS (SEQ ID NO:2)
TM3 (190-209)
IGMFFQSMATFFTGFIVGFT (SEQ ID NO:53)
Analog:
IGMFFQSMATFFTGFIVGFTGGD (SEQ ID NO:3)
TM4 (214-236)
LTLVILAISPVLGLSAAVWAKILS (SEQ ID NO:54)
Analog:
SSDDTLTLVILAISPVLGLSAAV (SEQ ID NO:4)
TM5 (297-323)
ISIGAAFLLIYASYALAFWYGTTLVLS (SEQ ID NO:55)
Analog 1 (active, but not very soluble):
ISIGAAFLLIYASYALAFWYGTTDD (SEQ ID NO:56)
Analog 2 (solubility was improved by truncating hydrophobic end of "A region" and adding serine and glycine residues at extracellular end):
LLIYASYALAFWYGTTLVLSGEGSSG (SEQ ID NO:5)
TM6 (326-352)
YSIGQVLTVFFSVLIGAFSVGQASPSI (SEQ ID NO:57)
Analog 1 (most active):
DSGEYSIGQVLTVFFSVLIGAFSV (SEQ ID NO:6)
Analog 2:
DDGSGEYSIGQVLTVFFSVLIGAFSVG (SEQ ID NO:58)
Analog 3:
DDDSGEYSIGQVLTVFFSVLIGAFSVG (SEQ ID NO:59)
TM7 (708-728)
WPYFVVGVFCAIINGGLQPAFAIIFSKII (SEQ ID NO:60)
Analog:
AIINGGLQPAFAIIFSKIIGDD (SEQ ID NO:7)
TM8 (754-776)
LFSLLFLALGIISFITFFLQGFTF (SEQ ID NO:61)
Analog:
GDDSLFSLLFLALGIISFITF (SEQ ID NO:8)
TM9 (833-853)
LAVITQNIANLGTGIIISFIY (SEQ ID NO:62)
Analog:
LAVITQNIANLGTGIIISFIYGDD (SEQ ID NO:9)
TM10 (854-874)
GWQLTLLLLAIVPIIAIAGVV (SEQ ID NO:63)
Analog:
GDDGWQLTLLLLAIVPIIA (SEQ ID NO:10)
TM11 (937-957)
IFGITFSFTQAMMYFSYAGCF (SEQ ID NO:64)
Analog:
IFGITFSFTQAMMYFSYAGCFDD (SEQ ID NO:11)
TM12 (974-995)
VLLVFSAVVFGAMAVGQVSSFA (SEQ ID NO:65)
Analog:
DDDLMSFEDVLLVFSAVVFGAMAVG (SEQ ID NO:12)

Example 5

This Example sets forth the results of studies of the effect of ABC transporter TM polypeptides on cells expressing a targeted ABC transporter.

a. Studies Using Various TM Analogs

P-gp-expressing KB 8-5 cells were trypsinized, washed with 15 mL Iscove's modified Dulbecco's medium (IMEM), supplemented with 5% fetal bovine serum (FBS), and resuspended in the same medium. Five hundred thousand cells were incubated in 5 mL of IMEM containing 5% FBS and 0.5 µg/mL of rhodamine 123, with or without 5 µM cyclosporin A or 5 µM TM peptide 1, 2, 6, 11, or 12 for 40 min at 37° C. in the dark. After the incubation, the cells were pelleted by centrifugation at 200×g and incubated further in their respective rhodamine-free media (+/−TM peptide) for an additional 45 min at 37° C. in the dark. Cells were then pelleted and resuspended in 400 µL of phosphate-buffered saline without Ca+2 or Mg+2 and immediately analyzed by fluorescence activated cell sorting (FACS). All of the peptides inhibited rhodamine efflux at the 5 µM concentration used in this assay.

b. Study Using TM5 Analog

Analog 2 of TM5 (the sequence of this analog is set forth in Example 4, above) was tested in vitro at a concentration of 5 micromolar. The analog was found to produce the same degree of inhibition of rhodamine 123 efflux from MDR1 expressing cells as 5 micromolar cyclosporin, which is considered to inhibit P-glycoprotein completely at this concentration. Unlike cyclosporin, the analog was totally non-toxic to the cells.

Example 6

This Example shows a dose/response study on an ABC transporter TM polypeptide.

Incubations of KB 8-5 cells were carried out as described in the previous Example, except that varying concentrations of the analog called TM 6 (see Example 4, supra) were used as the TM polypeptide. The positive control for inhibition of P-gp was 5 µM cyclosporin A. The data showed that TM 6 inhibited P-gp in a dose dependent manner. Although TM 6 was not as powerful an inhibitor as cyclosporin A in this assay, it was very effective in reducing the activity of the MDR1 ABC transporter, as measured by the ability of the cell to efflux substrate.

These results demonstrate the ability of externally added molecules to compete for interaction between transmembrane domains of ABC transporters and thereby to disrupt substrate transport.

Example 7

This Example sets forth an assay for determining whether a given analog sensitizes tumor cells to a standard chemotherapeutic agent, presumably by decreasing the ability of the cells to efflux the chemotherapeutic agent from the cells.

To test the ability of the analogs of the invention to make tumor-derived cells more sensitive to chemotherapeutic agents, the toxicity of the drugs is tested in the presence and absence of P-gp inhibitor. Human colon cancer cells HCT15 express high levels of P-gp, which makes them resistant to the anti-cancer drug adriamycin. The toxicity is assessed by a standard procedure that utilizes sulforhodamine-staining of the treated cells (Skehan et al., J Natl Cancer Inst 82(13): 1107-12 (1990)). The cells are seeded on 96-well plates (Nunc) a day before the assay, and cultured in the presence of various concentrations of adriamycin. The cells in some wells are cultured without the analog being tested as a control, and cells in other wells are exposed to the analog, with an increasing concentration of the analog being employed in each succeeding well. The cells are incubated for four days under 5% $CO_2$ at 37° C. The cultures are fixed for 1 hour by addition of ice-cold 50% trichloroacetic acid to give to a final concentration of 10%. Fixed cells are rinsed with water and stained for 20 min with 0.4% sulforhodamine B in 0.1% acetic acid. The wells are washed with 0.1% acetic acid and left to dry overnight. The absorbed sulforhodamine B is dissolved in unbuffered 1% Tris solution in water (pH 9.5-10). The absorbency of extracted sulforhodamine at 540 nm is measured on a plate reader.

The MDR1 TM6 analog described in Example 4 was employed in the assay described in this Example. When tested at a concentration of 1 µM, TM6 caused the $IC_{50}$ of adriamycin to shift from 150±10 nM to 80±8 nM.

Example 8

This Example sets forth a protocol for assaying for the ability of an ABC TM analog to inhibit activity of an ABC transporter. In particular, the assay can determine the ability of an agent to inhibit anti-P-gp activity.

NIH/3T3 cells stably transfected with P-gp cDNA were grown to almost confluency in multi-well plates. Ninety six, twenty four, and six well plates were all used in separate tests. The media was aspirated from the wells and was replaced in each well with medium containing 1 µg/ml of rhodamine 123 and either a negative control (medium without a known or potential inhibitor, a positive control, cyclosporine, or a compound being tested for inhibition activity, at a chosen concentration. The compound being tested for activity as an inhibitor was tested at 5 different concentrations. After a 40 min incubation in a $CO_2$-incubator, the medium in each well was replaced with one that did not contain rhodamine, but did contain the same control or compound being tested as a potential inhibitor as was originally used in that well, and the plates were returned to the incubator for an additional 40 min. The cells were rinsed with phosphate buffered saline and fixed/extracted with methanol for 30 min. For six-well and twenty four-well plates, 1 ml per well of methanol was used, for 96-well plates, 0.1 ml of methanol was used. For six-well and 24-well plates, the supernatant was aspirated and fluorescence was measured in a cuvette in a conventional fluorometer (FluoroMax-2, Jobin Yvon Horiba, Edison, N.J.). The fluorometer was set 490 m to excite the fluorophor and at 528 nm to read the fluorescence. For 96-well plates, the measurements were performed directly on the plates of the assay (black wall Costar 96-well plates) utilizing the top reading optics of a FLUOstar Galaxy multi-well reader (BMG Labtechnologies). The reader was set at 485 nm to excite the fluorophor and at 520 nm to read the fluorescence. Five wells were used for each inhibitor concentration and cyclosporin A was used used as a positive control. The total time to perform the assay was less than 2 hours on pre-grown cells and the results were very reproducible.

It is understood that the examples and embodiments described herein are for illustrative purposes only and that various modifications or changes in light thereof will be suggested to persons skilled in the art and are to be included within the spirit and purview of this application and scope of the appended claims. All references cited herein, including journal articles, books, and abstracts, published or corresponding U.S. or foreign patent applications, issued U.S. or foreign patents, and any other references, are incorporated by reference herein, including all data, tables, figures, and text presented in the cited references.

What is claimed is:

1. An isolated ATP-binding cassette (ABC) transporter protein-inhibiting peptide, wherein
   (a) said ABC transporter protein comprises a sequence of amino acid residues which forms a plurality of transmembrane domains and extracellular domains when said protein is present in a cell plasma membrane,
   (b) said ABC transporter protein-inhibiting peptide has a first end and a second end, and said peptide has at said first end a group that is negatively charged under physiological conditions and at said second end has a group that is neutrally charged under physiological conditions;
   (c) said first end comprises 1 to 6 amino acid residues, of which at least 1 is negatively charged at physiological pH;
   (d) said second end consists of a sequence of amino acid residues, which sequence (i) consists of the sequence of amino acid residues of a transmembrane domain of said ABC transporter protein, and, optionally, further comprises between said first and second ends, one or more residues from the amino acid residue sequence of the extracellular domain of said ABC transporter protein directly adjacent to said transmembrane domain, (ii) consists of the sequence of ten or more amino acid residues of said transmembrane domain and, optionally, further comprises between said first and second ends, one or more residues from the amino acid residue sequence of the extracellular domain of said ABC transporter protein directly adjacent to said transmembrane domain or, (iii) consists of a sequence with at least 90% sequence identity to the sequence of (i) or (ii);
   (e) said peptide spontaneously inserts into a plasma membrane of a cell in the same orientation as the ABC transporter protein transmembrane domain with which it shares sequence identity when said ABC transporter protein is present in said plasma membrane of said cell; and
   (f) said peptide inhibits efflux of a substrate of said ABC transporter protein from cells expressing said ABC transporter protein when said cells are contacted with said peptide.

2. The peptide of claim 1, wherein the negatively charged group at the first end of the peptide comprises one to three amino acid residues that are negatively charged under physiological conditions.

3. The peptide of claim 1, wherein the negative charge of the group at the first end of the peptide is provided by a carboxyl, phosphate, borate, sulfonate or sulfate functional group.

4. A peptide of claim 1, wherein the ABC transporter protein is MDR1, and further wherein said peptide has a sequence selected from the group of sequences consisting of:
   VGTLAAIIHGAGLPLMMLVFGEDD (SEQ ID NO:1);
   DDYAYYYSGIGAGVLVAAYIQVS (SEQ ID NO:2);
   IGMFFQSMATFFTGFIVGFTGGD (SEQ ID NO:3);
   SSDDTLTLVILAISPVLGLSAAV (SEQ ID NO:4);
   LLIYASYALAFWYGTTLVLSGEGSSG (SEQ ID NO:5);
   DSGEYSIGQVLTVFFSVLIGAFSV (SEQ ID NO:6);
   AIINGGLQPAFAIIFSKIIGDD (SEQ ID NO:7);
   GDDSLFSLLFLALGIISFITF (SEQ ID NO:8);
   LAVITQNIANLGTGIIISFIYGDD (SEQ ID NO:9);
   GDDGWQLTLLLLAIVPIIA (SEQ ID NO:10);
   IFGITFSFTQAMMYFSYAGCFDD (SEQ ID NO:11);
   DDDLMSFEDVLLVFSAVVFGAMAVG (SEQ ID NO:12); and,
   DEDVLLVFSAVVFGAMAVG (SEQ ID NO:50).

5. A peptide of claim 4, wherein the peptide is LLIYASYALAFWYGTTLVLSGEGSSG (SEQ ID NO:5).

6. An ABC transporter protein-inhibiting peptide of claim 4, wherein the biological activity of MDR1 modulated by said peptide is efflux of a cytotoxin from cytoplasm of a cell expressing MDR1.

7. An ABC transporter protein-inhibiting peptide of claim 4, wherein the cytotoxin whose efflux is modulated by said peptide is selected from the group consisting of topotecan, mitoxantrone, doxorubicin, daunorubicin, etoposide, vincristine, and vinblastine.

8. A composition comprising an ABC transporter-inhibiting peptide of claim 4 in a pharmaceutically acceptable carrier.

9. A method of inhibiting the efflux of a substrate of ATP-binding cassette ("ABC") transporter protein MDR1 from a cell that expresses said transporter, said method comprising contacting said cell in vitro with a peptide of claim 4.

10. A method of claim 9, wherein the peptide of claim 1 is present in a concentration of about 0.01 to about 100 micromolar.

11. The peptide of claim 1, wherein said ABC transporter protein is BCRP/MXR/ABCP and further wherein said peptide has a sequence selected from the group of sequences consisting of:
   IIVTVVLGLVIGAIYFGLKNDSD (SEQ ID NO:13);
   DAGVLFFLTTNQCFSSVSAVELFVV (SEQ ID NO:14);
   LLPMRMLPSIIFTCIVYFMLGLKPDD (SEQ ID NO:15);
   DDAFFVMMFTLMMVAYSASSMALAI (SEQ ID NO:16);

LLMTICFVFMMIFSGLLVNLDD (SEQ ID NO:17); and
DDNHVALACMIVIFLTIAYLKLLF (SEQ ID NO:18).

12. A composition comprising the BCRP/MXR/ABCP-inhibiting peptide of claim 11 in a pharmaceutically acceptable carrier.

13. A method of inhibiting efflux of a substrate of ATP-binding cassette ("ABC") transporter protein BCRP/MXR/ABCP, said method comprising contacting in vitro a cell that expresses said BCRP/MXR/ABCP with a peptide of claim 11.

14. The method of claim 13, wherein the peptide of claim 1 is present in a concentration of about 0.01 to about 100 micromolar.

15. The ABC transporter protein-inhibiting peptide of claim 1, wherein the substrate of said ABC transporter protein is a chemotherapeutic agent.

16. The ABC transporter protein-inhibiting peptide of claim 15, wherein the chemotherapeutic agent whose efflux is inhibited by said peptide is selected from the group consisting of topotecan, mitoxantrone, doxorubicin, daunorubicin, etoposide, vincristine, and vinblastine.

17. A peptide of claim 1, wherein the ABC transporter protein is MRP1 and further wherein said peptide has a sequence selected from the group of sequences consisting of:
GIFLAPVFLVSPTLLGITTIDD (SEQ ID NO:19);
DDSSGIMLTFWLVALVCALAIL (SEQ ID NO:20);
FYVYFSLLLIQLVLSCFSDRSPLDD (SEQ ID NO:21);
DDGYFYTVLLFVTACLQTLVL (SEQ ID NO:22);
INMIWSAPLQVILALYLLWLDD (SEQ ID NO:23);
DDGPSVLAGVAVMVLMVPVNAV (SEQ ID NO:24);
TPFLVALCTFAVYVTIDENNILD (SEQ ID NO:25);
DDFNILRFPLNILPMVISSIV (SEQ ID NO:26);
AIGLFISFLSIFLFMCNHVSDD (SEQ ID NO:27);
DDSQGIAVFGYSMAVSIGGILA (SEQ ID NO:28);
VIGACIVILLATPIAAIIIPDD (SEQ ID NO:29); and
DDECVGNCIVLFAALFAVIS (SEQ ID NO:30).

18. An ABC transporter-inhibiting peptide of claim 17, wherein the biological activity of MRP1 inhibited by said peptide is efflux of a chemotherapeutic agent from cytoplasm of a cell expressing MRP1.

19. An ABC transporter-inhibiting peptide of claim 18, wherein the chemotherapeutic agent whose efflux is inhibited by said peptide is selected from the group consisting of topotecan, mitoxantrone, doxorubicin, daunorubicin, etoposide, vincristine, and vinblastine.

20. A composition comprising an ABC transporter protein-inhibiting peptide of claim 17 in a pharmaceutically acceptable carrier.

21. A method of inhibiting efflux of a substrate of ATP-binding cassette ("ABC") transporter protein MRP1, said method comprising contacting in vitro a cell that expresses said ABC transporter with a peptide of claim 17.

22. A method of claim 21, wherein the concentration of the peptide is about 0.01 to about 100 micromolar.

23. A method of claim 22, wherein the substrate whose efflux is inhibited a chemotherapeutic agent.

24. A peptide of claim 1, wherein the ABC transporter protein is MRP2, and further wherein said peptide has a sequence selected from the group of sequences consisting of:
VLVWIPLGFLWLLAPWQLLHVDD (SEQ ID NO:31);
DDQVFVGFLLILAAIELALVLT (SEQ ID NO:32);
PAVRYTNPSLYLGTWLLVLLIDD (SEQ ID NO:33);
DDFLSLFWILSILCGTFQFQTLI (SEQ ID NO:34);
NLAYSCLFFISYGFQILILIFSAFSED (SEQ ID NO:35);
DDKTFYMVLLKSFLLKLVNDIFTFV (SEQ ID NO:36);
TYLWIGYLCAILLFTAALIQSFDD (SEQ ID NO:37);
DDTNFMHMLWSSVLQIVLSIFFLW (SEQ ID NO:38);
LGPSVLAGVGVMVLVIPINAILDD (SEQ ID NO:39);
DDQLQCVVIFVFQLTPVLVSVVTFSV (SEQ ID NO:40);
FTSITLFNILRFPLSMLPMMIDD (SEQ ID NO:41);
DDQAIGLFSIFFIILAFVMNSVAFI (SEQ ID NO:42);
LGLAQGIFVFIAHFWSAFGFVDD (SEQ ID NO:43);
DDSTLVMICMATPVFTIIVIPLG (SEQ ID NO:44);
AIRLELVGNLTVFFSALMMVIDD (SEQ ID NO:45); and
DDSSLTNCLFRILEAAGGQIII (SEQ ID NO:46).

25. An ABC transporter protein-inhibiting peptide of claim 24, wherein the substrate of MRP2 is a chemotherapeutic agent.

26. An ABC transporter protein-inhibiting peptide of claim 25, wherein the chemotherapeutic agent whose efflux is modulated by said peptide is selected from the group consisting of topotecan, mitoxantrone, doxorubicin, cisplatin, CPT-11, SN-38, and camptothesins.

27. A composition comprising the MRP24-inhibiting peptide of claim 24 in a pharmaceutically acceptable carrier.

28. A method of inhibiting efflux of a substrate of ATP-binding cassette ("ABC") transporter MRP2, said method comprising contacting in vitro a cell that expresses said ABC transporter with a peptide of claim 24.

29. A method of claim 28, wherein the peptide of claim 24 is present in a concentration of about 0.01 to about 100 micromolar.

30. A composition comprising the ABC transporter protein-inhibiting peptide of claim 1 in a pharmaceutically acceptable carrier.

31. A method of inhibiting the efflux of a substrate of an ATP-binding cassette ("ABC") transporter protein in a cell that expresses said transporter, said method comprising contacting said cell in vitro with the peptide of claim 1, wherein said contacting of said cell with said peptide inhibits efflux of a substrate of said ABC transporter protein from said cell.

32. The method of claim 31, wherein the peptide of claim 1 is present in a concentration of about 0.01 to about 100 micromolar.

33. The method of claim 31, wherein the substrate of said ABC transporter protein is a chemotherapeutic agent.

34. The method of claim 33, wherein the chemotherapeutic agent whose efflux is inhibited by said peptide is selected from the group consisting of topotecan, mitoxantrone, doxorubicin, daunorubicin, etoposide, vincristine, and vinblastine.

35. The peptide of claim 1, further wherein said peptide has, between said first and second ends, one or more residues from the amino acid residue sequence of the extracellular domain of BCRP/MXR/ABCP directly adjacent to said transmembrane domain.

36. The peptide of claim 1, wherein said second end of said peptide has at least 95% sequence identity to (i) or (ii).

37. The peptide of claim 1, wherein said second end of said peptide has the sequence of said transmembrane domain of the ABC transporter protein.

38. The peptide of claim 1, wherein said transmembrane domain of said ABC transporter protein has a sequence of amino acid residues and said second end of said peptide consists of the sequence of 16 or more amino acid residues of said transmembrane domain.

39. The peptide of claim 1, further wherein said peptide has, between said first and second ends, one to six residues from the amino acid residue sequence of the extracellular domain of said ABC transporter protein directly adjacent to said transmembrane domain.

* * * * *